United States Patent
Liu

(10) Patent No.: US 10,216,895 B2
(45) Date of Patent: Feb. 26, 2019

(54) RARE VARIANT CALLS IN ULTRA-DEEP SEQUENCING

(71) Applicant: Roche Molecular Systems, Inc., Pleasanton, CA (US)

(72) Inventor: Wei-Min Liu, Dublin, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 610 days.

(21) Appl. No.: 14/709,958

(22) Filed: May 12, 2015

(65) Prior Publication Data

US 2015/0324519 A1    Nov. 12, 2015

Related U.S. Application Data

(60) Provisional application No. 61/991,820, filed on May 12, 2014.

(51) Int. Cl.
*G01N 33/48* (2006.01)
*G06F 19/22* (2011.01)
*G06F 19/18* (2011.01)

(52) U.S. Cl.
CPC ............. *G06F 19/22* (2013.01); *G06F 19/18* (2013.01)

(58) Field of Classification Search
CPC ........................................................ G06F 19/22
USPC ............................................................. 702/19
See application file for complete search history.

(56) References Cited

U.S. PATENT DOCUMENTS

2014/0066317 A1* 3/2014 Talasaz ................ C12Q 1/6869
506/2

FOREIGN PATENT DOCUMENTS

WO     WO2014014498 A1    1/2014

OTHER PUBLICATIONS

"Somatic Variant Caller," Technical Notes: Infomatics, Illumina, Inc., copyright 2012-2015, 2 pages.

Diaz et al., "Liquid Biopsies: Genotyping Circulating Tumor DNA," Journal of Clinical Oncology 32:579-587 (Feb. 2014).
Diehl et al., "Circulating mutant DNA to assess tumor dynamics," Nature Medicine 14:985-990 (Sep. 2008).
Kidess et al., "Circulating tumor cells versus tumor-derived cell-free DNA: rivals or partners in cancer care in the era of single-cell analysis?," Genome Medicine 5:70 (Aug. 2013), 4 pages.
Lachin, *Biostatistical Methods: The Assessment of Relative Risks*, 2nd edition, New Jersey: John Wiley, copyright 2011, pp. vii-xxiii and 1-42.
Li et al., "Mapping short DNA sequencing reads and calling variants using mapping quality scores," Genome Research 18:1851-1858 (Nov. 2008).
Marth et al., "A general approach to single-nucleotide polymorphism discovery," Nature Genetics 23:452-456 (Dec. 1999).
Medvedev et al., "Maximum Likelihood Genome Assembly," Journal of Computational Biology 16:1101-1116 (2009).
Pevzner et al., "De novo repeat classification and fragment assembly," Genome Research 14:1786-1796 (2004).
Li M et al., A new approach for detecting low-level mutations in next-generation sequence data, Genome Biology, Jan. 1, 2012, p. R34: 1-15, XP055204408, vol. 13, No. 6, BioMed Central.
Li M. et al., A new approach for detecting low-level mutations in next-generation sequence data: Additional data file 2: Supplemental materials and methods, Genome Biology, May 23, 2012, XP055205290.
O'Fallon et al. 2013, A support vector machine for identification of single-nucleotide polymorphisms from next-generation sequencing data, Bioinformatics, Apr. 24, 2013, pp. 1-7, XP055205142, Oxford University Press.
Yang X. et al., V-Phaser 2: variant inference for viral populations, BMC Genomics, Jan. 1, 2013, p. 674: 1-10, vol. 14, No. 1, BioMed Central.
Chinese Office Action dated Jul. 13, 2018 received in corresponding Chinese Patent Application No. 201580024749.2.

* cited by examiner

*Primary Examiner* — Jerry Lin
(74) *Attorney, Agent, or Firm* — Kilpatrick Townsend and Stockton LLP

(57) ABSTRACT

Accurate variant calling methods for low frequency variants are provided. Sequence reads of targeted ultra-deep sequencing are received and aligned to a reference sequence. Read depths and variant counts for variants of the same class at each location where the reference allele exists on the reference sequence are determined for each sample-amplicon. Based on the read depths and variant counts, a probability value indicating the confidence level that a specific variant at a specific location is a true positive is calculated using methods such as a statistical model based method and a localized method using a reference sample. The probability value is then compared with a threshold level to determine whether the detected variants are true positives.

11 Claims, 17 Drawing Sheets

FIG. 12

| Q | qnorm | qchisq | Q | qnorm | qchisq | Q | qnorm | qchisq | Q | qnorm | qchisq |
|---|---|---|---|---|---|---|---|---|---|---|---|
| 3.5 | 0.1340 | 0.0180 | 35.5 | 3.4485 | 11.8923 | 67.5 | 5.0913 | 25.9211 | 99.5 | 6.3436 | 40.2417 |
| 4.5 | 0.3724 | 0.1387 | 36.5 | 3.5102 | 12.3216 | 68.5 | 5.1348 | 26.3657 | 100.5 | 6.3790 | 40.6916 |
| 5.5 | 0.5774 | 0.3334 | 37.5 | 3.5710 | 12.7519 | 69.5 | 5.1779 | 26.8106 | 101.5 | 6.4142 | 41.1416 |
| 6.5 | 0.7592 | 0.5764 | 38.5 | 3.6308 | 13.1830 | 70.5 | 5.2207 | 27.2557 | 102.5 | 6.4492 | 41.5917 |
| 7.5 | 0.9237 | 0.8532 | 39.5 | 3.6898 | 13.6148 | 71.5 | 5.2632 | 27.7010 | 103.5 | 6.4840 | 42.0419 |
| 8.5 | 1.0747 | 1.1550 | 40.5 | 3.7480 | 14.0475 | 72.5 | 5.3053 | 28.1465 | 104.5 | 6.5186 | 42.4923 |
| 9.5 | 1.2149 | 1.4760 | 41.5 | 3.8054 | 14.4809 | 73.5 | 5.3472 | 28.5923 | 105.5 | 6.5531 | 42.9427 |
| 10.5 | 1.3462 | 1.8122 | 42.5 | 3.8620 | 14.9149 | 74.5 | 5.3887 | 29.0383 | 106.5 | 6.5874 | 43.3932 |
| 11.5 | 1.4699 | 2.1606 | 43.5 | 3.9179 | 15.3497 | 75.5 | 5.4300 | 29.4844 | 107.5 | 6.6215 | 43.8438 |
| 12.5 | 1.5872 | 2.5192 | 44.5 | 3.9730 | 15.7850 | 76.5 | 5.4709 | 29.9308 | 108.5 | 6.6554 | 44.2945 |
| 13.5 | 1.6989 | 2.8863 | 45.5 | 4.0275 | 16.2209 | 77.5 | 5.5116 | 30.3774 | 109.5 | 6.6892 | 44.7453 |
| 14.5 | 1.8057 | 3.2606 | 46.5 | 4.0814 | 16.6574 | 78.5 | 5.5519 | 30.8241 | 110.5 | 6.7228 | 45.1962 |
| 15.5 | 1.9082 | 3.6412 | 47.5 | 4.1345 | 17.0945 | 79.5 | 5.5921 | 31.2710 | 111.5 | 6.7563 | 45.6472 |
| 16.5 | 2.0068 | 4.0271 | 48.5 | 4.1871 | 17.5320 | 80.5 | 5.6319 | 31.7181 | 112.5 | 6.7896 | 46.0983 |
| 17.5 | 2.1019 | 4.4178 | 49.5 | 4.2391 | 17.9701 | 81.5 | 5.6715 | 32.1654 | 113.5 | 6.8227 | 46.5494 |
| 18.5 | 2.1938 | 4.8127 | 50.5 | 4.2905 | 18.4086 | 82.5 | 5.7108 | 32.6129 | 114.5 | 6.8557 | 47.0007 |
| 19.5 | 2.2828 | 5.2113 | 51.5 | 4.3414 | 18.8476 | 83.5 | 5.7498 | 33.0605 | 115.5 | 6.8885 | 47.4520 |
| 20.5 | 2.3692 | 5.6133 | 52.5 | 4.3917 | 19.2870 | 84.5 | 5.7886 | 33.5082 | 116.5 | 6.9212 | 47.9034 |
| 21.5 | 2.4532 | 6.0182 | 53.5 | 4.4415 | 19.7269 | 85.5 | 5.8272 | 33.9562 | 117.5 | 6.9538 | 48.3549 |
| 22.5 | 2.5349 | 6.4259 | 54.5 | 4.4908 | 20.1671 | 86.5 | 5.8655 | 34.4043 | 118.5 | 6.9862 | 48.8065 |
| 23.5 | 2.6146 | 6.8360 | 55.5 | 4.5396 | 20.6077 | 87.5 | 5.9036 | 34.8525 | 119.5 | 7.0184 | 49.2582 |
| 24.5 | 2.6923 | 7.2484 | 56.5 | 4.5879 | 21.0488 | 88.5 | 5.9415 | 35.3009 | 120.5 | 7.0505 | 49.7099 |
| 25.5 | 2.7682 | 7.6629 | 57.5 | 4.6357 | 21.4901 | 89.5 | 5.9791 | 35.7494 | 121.5 | 7.0825 | 50.1617 |
| 26.5 | 2.8424 | 8.0793 | 58.5 | 4.6831 | 21.9318 | 90.5 | 6.0165 | 36.1980 | 122.5 | 7.1143 | 50.6136 |
| 27.5 | 2.9150 | 8.4974 | 59.5 | 4.7301 | 22.3739 | 91.5 | 6.0537 | 36.6468 | 123.5 | 7.1460 | 51.0654 |
| 28.5 | 2.9862 | 8.9171 | 60.5 | 4.7766 | 22.8163 | 92.5 | 6.0906 | 37.0958 | 124.5 | 7.1776 | 51.5174 |
| 29.5 | 3.0559 | 9.3384 | 61.5 | 4.8228 | 23.2590 | 93.5 | 6.1274 | 37.5448 | 125.5 | 7.2090 | 51.9696 |
| 30.5 | 3.1243 | 9.7610 | 62.5 | 4.8685 | 23.7020 | 94.5 | 6.1639 | 37.9940 | 126.5 | 7.2403 | 52.4217 |
| 31.5 | 3.1914 | 10.1850 | 63.5 | 4.9138 | 24.1452 | 95.5 | 6.2003 | 38.4433 | 127.5 | 7.2714 | 52.8742 |
| 32.5 | 3.2573 | 10.6102 | 64.5 | 4.9587 | 24.5888 | 96.5 | 6.2364 | 38.8927 | 128.5 | 7.3025 | 53.3259 |
| 33.5 | 3.3221 | 11.0365 | 65.5 | 5.0033 | 25.0327 | 97.5 | 6.2723 | 39.3423 | 129.5 | 7.3333 | 53.7788 |
| 34.5 | 3.3858 | 11.4639 | 66.5 | 5.0475 | 25.4768 | 98.5 | 6.3081 | 39.7919 | | | |

RARE VARIANT CALLS IN ULTRA-DEEP SEQUENCING

CROSS-REFERENCES TO RELATED APPLICATIONS

The present application claims priority from and is a non-provisional application of U.S. Provisional Application No. 61/991,820, entitled "Statistical scores for rare variant calls and estimation of target amount in ultra-deep sequencing" filed May 12, 2014, the entire contents of which are herein incorporated by reference for all purposes.

BACKGROUND

Nucleic acid sequencing determines an order of nucleotides present in a given DNA or RNA molecule. The demand for cheaper and faster sequencing methods has driven the development of next generation sequencing (NGS) methods. NGS platforms perform massively parallel sequencing, during which millions of fragments of DNA from multiple samples can be sequenced in unison, thus providing a much cheaper and higher throughput alternative to traditional Sanger sequencing. NGS can be used in whole-genome sequencing or targeted sequencing. With targeted sequencing, a subset of genes or defined regions in a genome are sequenced or predominantly sequenced, e.g., by amplifying target regions.

Ultra-deep sequencing is the sequencing of amplicons at a high depth of coverage with the goal of identifying the common and rare sequence variations. With sufficient depth of coverage, ultra-deep sequencing has the ability to fully characterize rare sequence variants down to less than 1%. Ultra-deep sequencing has been used to detect low-frequency HIV drug-resistant mutations, or identify rare somatic mutations in complex cancer samples. For tests such as non-invasive blood tests, the frequency of biomarker mutation could be lower than 1%. However, NGS is an error-prone process, and could have an error rate of close to 1% or higher depending on the sequencing depth, sample types, and sequencing protocols. Therefore, many current NGS software packages only report variants with 1% or higher frequency because false positives could appear for variants with frequencies of less than 1%. Yet, even for variants with low frequencies of, for example, less than 1%, true positives may exist. Methods and systems are therefore needed to detect true positives for variants with frequencies of less than about 1%.

BRIEF SUMMARY

Embodiments can provide methods, systems, and apparatuses for making more accurate variant calls based on sequencing reads of a sample, e.g., obtained from a targeted sequencing. For example, once sequence reads are received and aligned to a reference sequence, sequence reads having a variant at a location can be counted. A first variant frequency of a particular variant measured at one location of a sample can be compared to one or more second variant frequencies of the particular variant measured at other positions and/or from other samples. The second variant frequency can correspond to an expected value for sequencing errors for a sequencing run.

In some embodiments, a probability value indicating the confidence level that a variant is a true positive at a location can be calculated based on variant counts and total read counts at a plurality of locations in the target region in one or more samples. The probability value can then be compared with a threshold level to determine whether the detected variant is a true positive. In other embodiments, a difference in variant counts and total reads counts at a same location in a test sample and a reference sample (e.g., assumed to only have sequencing errors at the location) can be used to determine whether a variant is a true positive in a test sample.

According to one embodiment, a method can detect true positives for rare variants in a target region of a test sample. For each sample, variant frequencies for variants of a same variant class at locations where a reference allele exists on a reference sequence can be calculated using variant counts and total read counts. A distribution of the variant frequencies for variants of the same class can be used to determine the probability value of a variant at a location in the test sample with a determined variant frequency. Based on the probability value, the variant at the location in the test sample is classified as either a true positive (mutation) or a false positive.

In other embodiments, a method can detect true positives for rate variants in a target region of a test sample by using a comparison with one or more reference samples. A variant count and a wild type count for a specific variant at a specific location in the test sample can be determined from the aligned sequence reads, and compared with a variant count and a wild type count for the specific variant at the specific location in the one or more reference samples to determine a probability value. Based on the probability value, the specific variant at the specific location in the test sample is classified as either a true positive or false positive.

In one embodiment, a computer-implemented method of detecting low frequency variants in a target region in a first sample is provided. Herein, the method comprises (at a computer system) receiving a plurality of sequence reads obtained from sequencing DNA fragments from one or more samples, the one or more samples including the first sample, wherein the sequencing includes targeting the target region in the DNA fragments; aligning the plurality of sequence reads to the target region of a reference sequence; identifying a first candidate variant having a first allele at a first location of the target region based on sequence reads of the first sample differing from a reference allele at the first location of the reference sequence; determining a first variant frequency for the first allele at the first location based on sequence reads of the first sample that align to the first location of the reference sequence; identifying the first candidate variant as corresponding to a first variant class selected from a plurality of variant classes, each variant class of the plurality of variant classes corresponding to a different type of variant; identifying a set of second locations in the target region of the reference sequence that have the reference allele, wherein at least 50% of the other locations in the one or more samples exhibit a false positive for the first allele, and wherein the set of second locations includes the first location; at each of the set of second locations and for each of the one or more samples: determining a second variant frequency of the first allele based on sequence reads of the sample that align to the second location of the reference sequence, the second variant frequencies forming a statistical distribution; comparing the first variant frequency to a statistical value of the statistical distribution to determine a probability value of the first variant frequency relative to the statistical value of the statistical distribution; and comparing the probability value to a threshold value as part of determining whether the first candidate variant is a true positive in the first sample for the first allele, the threshold value differentiating between false positives and true positives for the first allele.

In certain embodiments, the reference sequence corresponds to a consensus sequence as determined from normal cells. In some embodiments, the one or more samples are derived from cell-free DNA fragments. In some embodiments, the one or more samples are derived from RNA of a biological sample. In some embodiments, the plurality of samples are sequenced in a single sequencing run. In other embodiments, the statistical value of the statistical distribution includes a mean value. In other embodiments, the probability value is a z-score, modified z-score, cumulative probability, Phred quality score, or modified Phred quality score. In other embodiments, the statistical distribution is the statistical distribution of logarithmic transformations of the second variant frequencies. In other embodiments, the threshold is determined using support vector machines classifier based on training data obtained from one or more sequencing runs. In other embodiments, the threshold is a function of variant frequency.

In another embodiment, a computer-implemented method of detecting a variant having a first allele at a first location in a target region in a first sample is provided. Herein, the method comprises (at a computer system): receiving a plurality of sequence reads obtained from sequencing DNA fragments from at least two samples, the at least two samples including the first sample, wherein the sequencing includes targeting the target region in the DNA fragments; aligning the plurality of sequence reads to the target region of a reference sequence; identifying whether the first allele exists at the first location in each sample of the at least two samples based on aligned sequence reads of each sample at the first location differing from a reference allele at the first location of the reference sequence; determining a variant count of the first allele at the first location and a wild type count of the reference allele at the first location for each sample of the at least two samples; selecting, from the at least two samples, at least one sample as a reference sample; comparing a first variant count of the first allele at the first location and a first wild type count of the reference allele at the first location for the first sample to a second variant count of the first allele at the first location and a second wild type count of the reference allele at the first location for the reference sample to determine a probability value of the variant having the first allele at the first location for the first sample; and comparing the probability value to a threshold value as part of determining whether the first allele at the first location in the first sample is a true positive for the first allele, the threshold value differentiating between false positives and true positives for the first allele at the first location.

In certain embodiments, the reference sample comprises two samples with lowest variant frequencies for the first allele at the first location among the at least two samples other than the first sample. In some embodiments, the probability value is determined using chi-squared cumulative distribution function. In some embodiments, the probability value is determined using Pearson proportion test. In some embodiments, the probability value is one or more of z-score, modified z-score, p-value, chi-squared value, cumulative probability value, and quality score. In some embodiments, the quality score is determined using a look-up table. In some embodiments, the threshold is determined using support vector machines classifier based on training data obtained from one or more sequencing runs. In some embodiments, the threshold is a function of variant frequency.

In another embodiment, a computer product comprising a non-transitory computer readable medium storing a plurality of instructions that when executed control a computer system to detect true variants in a target region of a first sample is provided. Herein, the instructions comprise receiving a plurality of sequence reads obtained from sequencing DNA fragments from one or more samples, the one or more samples including the first sample, wherein the sequencing includes targeting the target region in the DNA fragments; aligning the plurality of sequence reads to the target region of a reference sequence; identifying a set of sequence locations in the target region of the reference sequence that have a reference allele of variants in a variant class, wherein at least 50% of the sequence locations in the one or more samples exhibit a false positive for the variants in the variant class in the sequence reads, and wherein the set of sequence locations includes a first location; at each location of the set of sequence locations and for each sample of the one or more samples: determining a read count at each location for each sample; identifying candidate variants having variant alleles for the variants in the variant class based on sequence reads of each sample differing from the reference allele at the same location of the reference sequence, a total number of the candidate variants at each location in each sample being the variant count in each location for each sample; determining a variant frequency of variants in the variant class based on the read count and the variant count, the variant frequency for each location in each sample forming a statistical distribution, wherein the variant frequency at a first location in the set of sequence locations for the first sample is a first variant frequency; comparing the first variant frequency to a value of the statistical distribution to determine a probability value of the first variant frequency relative to the value of the statistical distribution; and comparing the probability value to a threshold value as part of determining whether candidate variants in the first sample are true positives, the threshold value differentiating between false positives and true positives for the variants in the variant class. In certain embodiments, the statistical distribution is the statistical distribution of a logarithmic transformation of the variant frequency at each location for each sample.

Other embodiments are directed to systems, apparatuses, and computer readable media associated with methods described herein.

A better understanding of the nature and advantages of the present invention may be gained with reference to the following definitions, detailed description, and the accompanying drawings.

DEFINITIONS

As used herein, the term "sample" or "biological sample" refers to any composition containing or presumed to contain nucleic acid. The nucleic acid can be from an animal (e.g., mammal, human), plant, microorganism, etc. The term sample includes purified or separated components of cells, tissues, or blood, e.g., DNA, RNA, proteins, cell-free portions, or cell lysates. A sample can also refer to other types of biological samples, e.g., skin, plasma, serum, whole blood and blood components (buffy coat), saliva, urine, tears, seminal fluid, vaginal fluids, aspirate or lavage, tissue biopsies, and other fluids and tissues, including paraffin embedded tissues. Samples also may include constituents and components of in vitro cultures of cells obtained from an individual, including cell lines. A "test sample" refers to the sample that is under test for detecting variants in the sample.

A "genomic segment" (also called "genomic fragment") is a nucleic acid molecule that is wholly or partially sequenced, where the molecule is from the genome of an organism. It may be a DNA segment (also called "DNA fragment") or a RNA segment (also called "RNA fragment"). The segment can be created by fragmenting larger pieces of a genome, e.g., by subjecting a cell to sonic waves. A genomic segment can be sequenced to provide a "sequencing read" (also called a "sequence read" or just a "read"). The sequencing read may be of the entire genomic segment or just part of the segment.

A "reference sample" (also called a "control sample") refers to a sample that serves as a reference, usually a known reference, for comparison to a test sample. For example, a test sample can be taken from an individual suspected of having cancer or a cancer-related mutation, and compared to a reference sample from a cancer-free individual or individual without a cancer-related mutation (negative control), or from an individual known to have cancer or a cancer-related mutation (positive control). A control can also represent an average value or a range gathered from a number of tests or results.

A "target region" is a region in the sequence being analyzed that may have diagnostic relevance. As an example, fragments including the target region can be amplified using primers and an amplification process or can be enriched using probes. A "reference sequence" (also simply called "reference") is any known sequence to which sequence reads are aligned. In various embodiments, the reference sequence may correspond to all or only part of a genome or a transcriptome for an organism. A reference sequence can also include genomes of more than one organism. For example, a sequence read could also be compared against a database of viruses, as such viruses could be in the sample.

A variant (also called a variation or mutation) refers to a difference between two sequences. A variant may be, for example, a change of one base to one or more other bases, an insertion of one or more bases, or a deletion of one or more bases. The base or bases at a location in the reference sequence may be referred to as reference allele, while the different base or bases (or insertion or deletion) at the same location on the test sample may be referred to as variant allele. For example, for single based substitution of A>C, A is the reference allele, and C is the variant allele. The reference allele may be wild type allele representing the most common genotype for the organism occurring in nature. A difference between a sequence read and a target region of a reference sequence can get counted, and a true mutation might be identified (e.g., if enough sequence read show the mutation).

The total number of same variant alleles, such as Cs for A>C variants, at a specific location on different sequence reads of a sample is referred to as variant count. The total number of reads of the specific location for a sample is referred to as read count. Variant frequency of a variant type or class, such as A>C, at a specific location for a sample is defined as the ratio of the variant count for the variant at the specific location over the read count at the specific location for the sample.

As used herein, the term "location" corresponds to one or more positions in a sequence (e.g., in a target region of a genome). Any length of nucleotides (or base pairs) may be present at a location, e.g., when there is a multi-base insertion.

Unless defined otherwise, technical and scientific terms used herein have the same meaning as commonly understood by a person of ordinary skill in the art. See, e.g., Pfaffl, Methods: The ongoing evolution of qPCR, vol. 50 (2010); van Pelt-Verkuil et al. Principles and Technical Aspects of PCR Amplification, Springer (2010); Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (1989).

BRIEF DESCRIPTION OF THE DRAWINGS

FIG. 12 illustrates a look-up table for efficient quality score estimation according to embodiments of the present invention.

DETAILED DESCRIPTION

Figure 1:
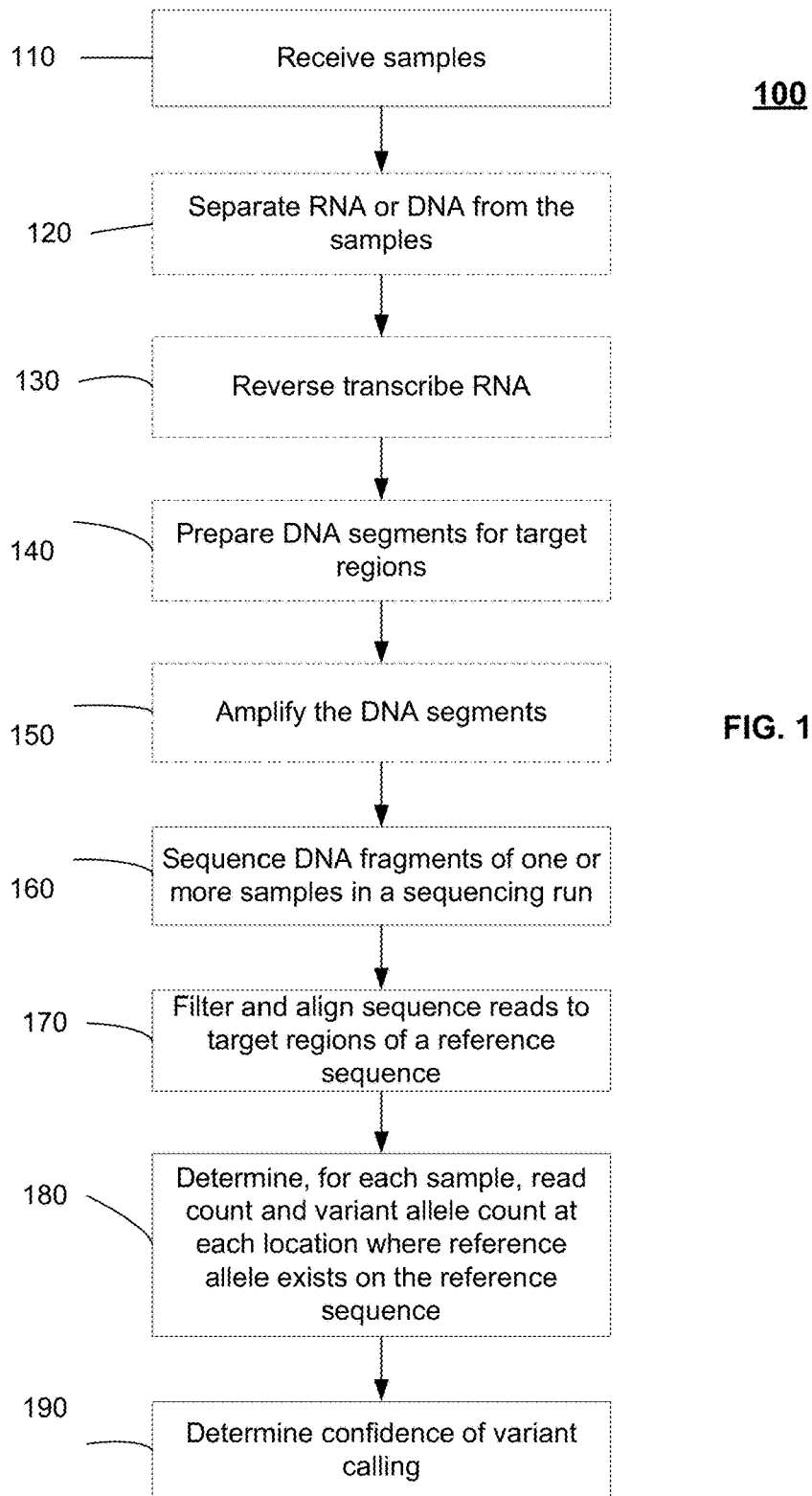
FIG. 1 is a flowchart illustrating genomic sequencing and variant calling using next generation sequencing (NGS) for targeted ultra-deep sequencing according to embodiments of the present invention.

Sequencing can be used to detect mutations of cancer or other diseases, and can also be developed as in vitro diagnostic (IVD) tests. It is desirable to develop these tests as non-invasive blood tests. However, in blood samples, the frequency of biomarker mutation is low. See, e.g., Kidess and Jeffrey, Circulating tumor cells versus tumor-derived cellfree DNA: rivals or partners in cancer care in the era of single-cell analysis? Genome. Med., 5:70 (2013), Diaz and Bardelli, Liquid biopsies: genotyping circulating tumor DNA, J. Clin. Oncol., 32:579-586 (2014); and Diehl et al., Nat Med., 14:985-990 (2008). Due to errors associated with the sequencing process, many NGS software packages only report variants with frequencies of 1% or higher because false positives appear when the threshold is set at or below 1%.

Embodiments of the present invention provide solutions to detect true positives for low frequency variants with variant frequencies below 1%, such as about 0.0025% to about 1%. Accurate variant calls can be based on sequencing reads of a sample, e.g., obtained from a targeted sequencing. For example, once sequence reads are received and aligned to a reference sequence, sequence reads having a variant at a location can be counted. A first variant frequency of a particular variant measured at one location of a sample can be compared to one or more second variant frequencies of the particular variant measured at other positions and/or from other samples. The second variant frequency can correspond to an expected value for sequencing errors for a sequencing run.

In some embodiments, a probability value indicating the confidence level that a variant is a true positive at a location can be calculated based on variant counts and total read counts at a plurality of locations in the target region in one or more samples. The probability value can then be compared with a threshold level to determine whether the detected variant is a true positive. In other embodiments, a difference in variant counts and total reads counts at a same location in a test sample and a reference sample (e.g., assumed to only have sequencing errors at the location) can be used to determine whether a variant is a true positive in a test sample.

I. Ultra-Deep Sequencing with Targeted Sequencing

A specific region of a genome can be analyzed efficiently using targeted sequencing. For example, genomic segments of a biological sample can be increased or amplified by cloning segments that correspond to a target region (e.g., using primers in an amplification process, such as polymerase chain reaction (PCR)) and/or using probes to preferentially capture segments that correspond to a target region. The genomic segments in the target-increased sample can be sequenced using massively parallel next generation sequencing (NGS) and analyzed to investigate possible mutations in the target region.

However, such a process can lead to errors. For example, in variant detection using high throughput next generation sequencing with a prior step of amplification or enrichment, it is possible that the amplicon/enriched library (target-increased sample) contains false positive reads. PCR can introduce point mutations and indels, and it can also generate recombinant sequences, or chimeras. In addition, the relative frequencies of genetic variants can be perturbed due to selective amplification bias during PCR. Additional single-base errors can occur during emulsion PCR. Sequencing itself may also introduce base substitution errors and indels. These errors can lead to incorrect mutation report and can provide misleading information for disease diagnosis. The false positives may be reduced by various methods, such as proper design of the primers and development of high fidelity enzymes. However, false positives still remain, and in many cases, the error rate could be significant, such as close to about 1% or more.

Even though the sequencing accuracy for each individual nucleotide can be relatively high, the large number of nucleotides in the genome means that if an individual genome is only sequenced once, there will be a significant number of sequencing errors. For example, for an error rate of 0.2% per base pair and a read length of 400 base pairs, the proportion of reads with at least one error is $1-(1-0.002)^{400}=0.551$, which means over 55% of the sequence reads could have at least one error. Therefore, to distinguish between sequencing errors and rare but true mutations, it is desirable to increase the sequencing accuracy by sequencing individual genomes a large number of times. For example, even if each sequence read contains a 1% error rate, the combination of eight identical reads that cover the location of the variant will produce a strongly supported variant detection with an error rate of $(10^{-2})^8$, or $10^{-16}$.

Depth in DNA sequencing refers to the number of times a nucleotide is read during the sequencing process. Deep sequencing indicates that the total number of reads is many times larger than the length of the sequence under study. Coverage is the average number of reads representing a given nucleotide in the reconstructed sequence. The term "deep" has been used for a wide range of depths, such as larger than 7 times, and the term "ultra-deep" generally refers to even higher coverage, such as larger than 100 times. Requirements for sequencing depth may depend on the variant type, the disease model, and the size of the regions of interest. Thus, for rare variants with variant frequencies of 1% or less, even higher coverage may be desired. The massively parallel NGS enables such ultra-deep sequencing for true variants detection. Nevertheless, generating greater depth of shorter reads does not resolve all the issues for rare variants detection.

II. Variant Calls in Ultra-Deep Sequencing

Variant calling is the process of identifying true differences between sequence reads of test samples and a reference sequence. Variant calling is important in sample characterization and disease diagnosis. However, variant calling is inherently difficult because somatic mutations often occur at very low frequencies. One goal of variant calling is to identify somatic variants with high confidence to minimize spurious false positives.

FIG. 1 illustrates a method 100 of genomic sequencing and variant calling using next generation sequencing (NGS) for targeted ultra-deep sequencing. As with other methods, embodiments can include all or some of the steps described, and some steps may be performed with a computer system. The results of method 100 may be used by a doctor in determining a diagnosis of an organism.

At block 110, samples containing polynucleotides to be sequenced and diagnosed are received, wherein the polynucleotides potentially include a target region to be sequenced. As defined above, the term "sample" refers to any composition containing or presumed to contain nucleic acid. The samples include nucleic acid molecules that are from the genome of the organism from which the samples are obtained. For example, the samples can include cells that contain a genome encoded in chromosomes. The samples may include one or more test samples. The samples may also include one or more reference or control samples. Some samples may be obtained from a patient who is being tested for mutations in particular regions of the genome. The samples may be obtained from a biopsy of a tumor that is being tested for cancer. The samples may include some normal cells, some cells at early stages of cancer progression, and some cells at later stages of cancer progression. The samples can be from different people or the same person (e.g., different biopsies), and may use different experimental conditions.

Optionally, at block 120, RNA or DNA is separated from the samples prior to sequencing. Methods for isolating nucleic acids from biological samples are known, for example, as described in Sambrook, and several kits are commercially available, for example, DNA Isolation Kit for Cells and Tissues, DNA Isolation Kit for Mammalian Blood, High Pure FFPET DNA Isolation Kit, High Pure RNA Isolation Kit, High Pure Viral Nucleic Acid Kit, and MagNA Pure LC Total Nucleic Acid Isolation Kit, all available from Roche. In some embodiments, the isolated nucleic acids include genomic DNA. In some embodiments, the isolated nucleic acids include circulating free DNA fragments (cfDNA). In some embodiments, the isolated nucleic acids include RNA, such as cellular mRNA or cfRNA.

In the case of RNA, at block 130, a reverse transcription reaction is carried out. For example, the RNA may be converted into a complementary DNA (cDNA) using a reverse transcriptase.

Optionally, at block 140, DNA segments may be prepared for sequencing. This may include fragmenting the DNA into smaller DNA segments including the target regions, ligating adapter sequences onto the ends of the DNA segments, and anchoring specific barcode sequences that identify the samples from which the DNA segments originated. A target region is a segment in the DNA that may have diagnostic relevance, e.g., to see if there is any cancer-related mutation. As examples, the target region can be about a few hundred bases, e.g., 150-250 bases, 150-400 bases, or 200-600 bases. In another embodiment, probes can be used to capture genomic segments that correspond to the target region. For example, probes that are designed to hybridize to the target region can be placed on a surface. Then, the genomic segments can be placed over the surface and the segments of the target region will preferentially be hybridized. The DNA of the samples can be fragmented, e.g., by sonication or other suitable methods to obtain smaller genomic segments. For example, genomic segments of 200-500 bases long can be obtained. For certain sequencing procedures, genomic segments of about this length are preferred. However, embodiments can use genomic segments of any length.

The genomic segments can be marked with a barcode or multiplex identifier (MID) sequence. For example, a sequence of 10 bases can be added (e.g., using a ligase) to the end of a genomic segment. In this manner, segments from various samples can be sequenced in parallel during a single sequencing run. The MID can be read as part of a sequence read, and sequence reads with the same MID can be attributed to a same sample and analyzed together. The MID can be used to de-multiplex or differentiate sequences reads from different samples.

At block 150, the DNA segments are optionally amplified or increased by an amplification process, such as PCR, SDA, and derivations thereof, to generate DNA segments, that is, amplification products, for sequencing. A DNA polymerase such as Taq or another thermostable polymerase can be used for amplification by PCR. See, e.g., Fakruddin et al., J Pharm Bioallied Sci. 5:245 (2013) for a review of amplification methods. These amplification products are defined based on primers used for the amplification. The primers are specific for a target region on the nucleic acid. Sequencing primers are typically designed based on the selection of amplification primers, such that the sequencing primers are specific for (specifically hybridize to) sequences within the amplification products. In some embodiments, the target regions may be enriched by a target enrichment process. Both amplification and enrichment processes could be performed. Forward and reverse primers can be used to amplify a target region. These forward and reverse primers can be of various length, e.g., about 15-30 bases long.

In some embodiments, the addition of the sample-specific MID can occur at different points. For example, the MID could be added after the amplification/enrichment before the samples are mixed together. In this way, different samples could be amplified or enriched for different target regions.

At block 160, DNA segments from one or more samples are sequenced in a massively parallel fashion in a single sequencing run. In the sequencing process, the clones of a same segment created in an amplification process can have its sequence determined separately (and counted later). In some embodiments, a single sequencing run can generate over one terabase of data. In some embodiments, more than about 3,000 reads per sample can be obtained. The number of reads may depend on the size of the sample, how much amplification was performed as a part of the target increase, and the bandwidth of the sequencing process (i.e., how much sequencing the apparatus is set for, e.g., how many beads are used). In one embodiment, the reads are about 150-250 bases long.

The sequencing process can be performed by various techniques on various NGS platforms, such as Roche 454, Illumina GA, and ABI SOLiD. In one embodiment, the DNA segments can undergo an amplification as part of the sequencing. In embodiments where an amplification process was used to create a target-increased sample, this amplification would be a second amplification step. The second amplification can provide a stronger signal (e.g., a fluorescent signal corresponding to a particular base: A, C, G, or T) than if the second amplification was not performed.

In one example of a sequencing process, amplified segments from block 150 (e.g., where amplification occurred in a solution) can each be attached to a bead. The attached segments can then be amplified on the bead, and one sequence read can be obtained from each bead. For embodiments that use a surface, a segment can be attached to a surface and then amplified to create a single cluster on the surface. A single sequence read can be obtained for each cluster. A sequence read can be for an entire length of a genomic segment or a part of the segment.

At block 170, the sequence reads can optionally be filtered to remove low quality reads and short reads, and the remaining sequence reads are aligned to a target region of a reference sequence. In some embodiments, reads with identical bases are combined so that they are considered a single sequence read. Thus, read counts for only unique read may be recorded. An average base score can be calculated at every base location for every unique read. A base score can measure how accurate a base call is on the sequence read. Using the base score, low quality reads can be removed. In some embodiments, reads that are shorter than a minimum value are removed as well.

By aligning, the process can compare the sequence reads to the target region of the reference sequence to determine the number of variations between the sequence reads and the reference sequence. As the alignment can be specific to only one or more target regions, the alignment can be fast because the entire genome does not have to be searched. Also, as the percentage of segments corresponding to a target region is increased, a substantial number of the reads would match favorably to the target region (e.g., relatively few variations).

In one embodiment, if multiple target regions are used, then a sequence read can be compared to all of the multiple target regions, and the target region that provides the best alignment can be identified. Different target regions can have different genes or different exons with a gene. Thus, the exon with the best alignment could be identified.

If a barcode or MID is used, it can be removed before aligning. The MID can be used to organize all of the reads for a particular sample into one group. In this manner, mutations from other samples will not impact the analysis of the particular sample. This grouping is referred to as de-multiplexing. As different samples may have different target regions, the MID can be used to determine which target region(s) of a reference sequence should be compared for the alignment.

At block 180, aligned sequence reads from the target region are used to identify mutations in the target region. As part of this step, the number of variant alleles (or variant count), the number of reference alleles (or wild type count), and thus the frequency of each variant at a sequence location for each sample can be determined. For example, for a particular position in a target region, the number of times a G mutation appears instead of a normal A can be counted. A percentage of times the G mutations is seen can be determined from the total reads that aligned to that position. In some embodiments, variations that occur together can be identified, and may be categorized as a part of a same mutation. For each sample, a sequencing depth for a target region can be determined from the number of reads passing any filters for that sample.

At block 190, variant calling is made based on the variant counts, the wild type counts, and/or the variant frequencies. In one embodiment, the variant frequency for a particular variant can be required to be greater than a threshold (abundance filter) to be considered an actual mutation. Table 1 shows minimal variant counts and variant frequencies calculated based on Poisson model that Illumina MSR somatic variant caller reports with default settings.

TABLE 1

Minimum variant count and minimum variant frequency to report for various depth

| Depth | MinCountToReport | Min % ToReport |
|---|---|---|
| 100 | 5 | 5 |
| 200 | 7 | 3.5 |
| 500 | 12 | 2.4 |
| 1000 | 19 | 1.9 |
| 2000 | 32 | 1.6 |
| 5000 | 68 | 1.36 |
| 10000 | 125 | 1.25 |
| 20000 | 235 | 1.175 |
| 50000 | 554 | 1.108 |
| 100000 | 1075 | 1.075 |

In some embodiments, a quality score indicating the confidence level that a variant is indeed present in the sample is provided and used to make a variant call. In some embodiments, the quality score may be used in combination with one or more of the variant count, the wild type count, and/or the variant frequency to make the variant call. A doctor could use the identified mutations to diagnose a predisposition to cancer or to identify a tumor as having cancer.

Figure 2:
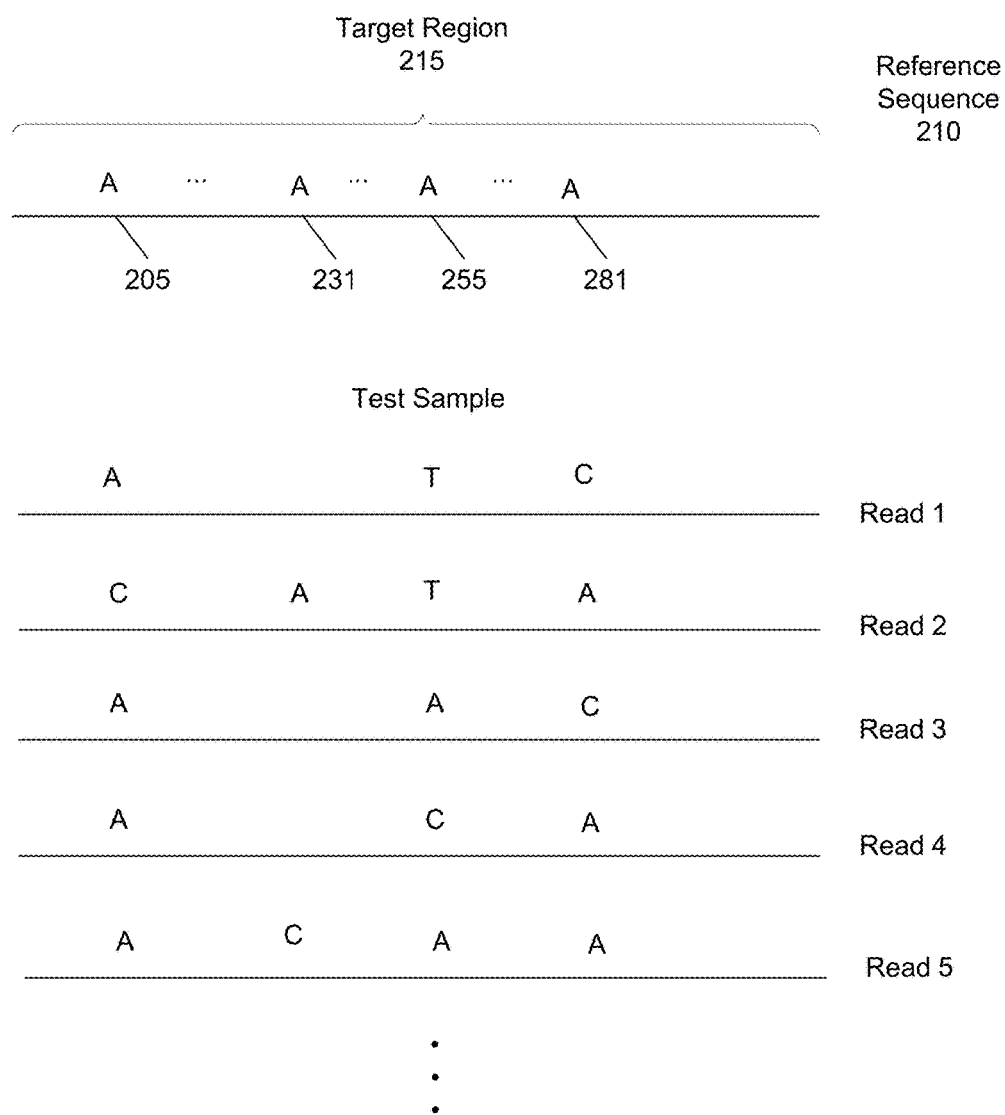
FIG. 2 illustrates sequence reads of a target region compared with a reference sequence, where variants of the same class and different class at different sequence locations are shown according to embodiments of the present invention.

FIG. 2 illustrates examples of sequence reads of a target region 215 in a test sample compared with a reference sequence 210, in which variants of a same class and different classes at various sequence locations are shown. FIG. 2 shows four example locations in a target region where the reference sequence has reference alleles of base A. Five sequence reads are explicitly shown for ease of illustration, but many more reads would be used, in practice. Reference sequence 210 is shown to have A at locations 205, 231, 255, and 281.

For location 205, in some sequence reads, A is detected, but in some sequence reads, C is detected. The detection of C indicates a potential A>C variant. The variant A>C is of a particular variant class. Other bases could be detected in the sequence reads not shown. The existence of other alleles could indicate other types of variants of other variant classes.

For location 231, in some sequence reads, A is detected; in some sequence reads, C is detected; in yet some other reads, nothing ("0") is detected at location 231. The detection of C indicates a potential variant of single-base substitution A>C. The detection of "0" indicates a potential variant of deletions.

For the base A in location 255, in some sequence reads, A is detected; in some sequence reads, C is detected; but in some other reads, T is detect. The detection of C indicates a potential variant of single-base substitution A>C. The detection of T indicates a potential variant of a different single-base substitution A>T.

For the base A in location 281, in some sequence reads, A is detected; in some sequence reads, C is detected at a different frequency. The detection of C at a different frequency indicates a potential variant of single-base substitution A>C with a different variant frequency.

Based on the sequence reads for the test sample, for each location, the number of wild type base A, the number of single-base substitution A>C, the number of single-base substitution A>T, and the number of deletions of A can be counted. The types of variants shown in FIG. 2 are for illustration purpose only. There may be various types of variants or mutations as described below in this disclosure.

III. Variant Calling Based on Statistical Distribution Model

In some embodiments of this disclosure, all variants observed in the NGS experiments can be reported. Because most observed low frequency variants may be false positive, in order to distinguish low frequency true positives from false positives, a distribution of false positive variants may be used to establish a variant calling quality score to determine how likely a variant is a true positive.

A. Mathematical Theory of the Statistical Model Based Variant Calling

FIGS. 3A-3D provide the underlying mathematical theory of statistical model based variant calling according to some embodiments of this invention. Because the false positive rates of variant calls depend on the sequence context and location, variants of the same class or type, such as A>C, at various locations in all samples may be compared together to make the variant calls based on a statistical distribution.

In some embodiments, simple variants in a sequencing run at different sequence locations may be divided into 20 classes. In every class, the majority of the variants are false positives. Parameters of the statistical distribution for every variant class can be calculated. The variant classes may be defined as follows:

(1) 12 single-base substitutions, including A>C, A>G, A>T, C>A, C>G, C>T, G>A, G>C, G>T, T>A, T>C and T>G;
(2) multiple-base substitutions, such as AC>GA;
(3) 1-2 bases deletions, such as AGT>AT or GCAT>GT;
(4) 3-base deletions, such as ATCGA>AA;
(5) 4-5 bases deletions, such as GACCTA>GA or TGCGCGA>TA;
(6) 6 or more bases deletions, such as ATCCTCAG>AG;
(7) 1-2 bases insertions, such as AT>AAT or GC>GTAC;
(8) 3 or more bases insertions, such as GC>GTAAC or AC>AGATGC; and
(9) other simple mutations, such as a single-base substitution A>C followed immediately by a 1-base deletion, e.g., the original reference bases are AT and the mutant base is C, i.e., AT>C. Such mutation AT>C may also be interpreted as a deletion of A followed by single-base substitution T>C.

As used here, a simple mutation is a mutation bounded by two matching base pairs without any matching base pair within it. For example, in aATg and aCg, simple mutation AT>C is bounded by a matching pair a-a and a matching pair g-g, where lower case letters are used for the matching pairs. But in aAcGg and aCcTg, AcG>CcT is not a simple mutation because there is a matching pair c-c in it. Thus, AcG>CcT is a complex mutation consisting of two simple mutations A>C and G>T.

In some embodiments, the variant frequency of variants of a same class, such as A>C, at various locations in the target region where the reference allele (e.g., base A for variant type A>C) exists in the reference sequence for one or more samples may be used to form a statistical distribution for the variant class. For example, as shown in FIG. 2, the variant frequency of single-base substitution A>C at each of location 205, location 231, location 255, location 281, and other locations in the target region where A exists in the reference sequence for a sample may be a data point for the statistical distribution for variant class A>C. The variant frequency of single-base substitution A>C at each of location 205, location 231, location 255, location 281, and other locations in the target region where A exists in the reference sequence for each of other samples sequenced in the same sequencing run as the test sample may also be a data point for the statistical distribution for variant class A>C. On the other hand, the variant frequency of a different variant class, such as single-base substitution A>T or a single-base deletion A>0, at each of location 205, location 231, location 255, location 281, and other locations in the target region where A exists in the reference sequence for each sample sequenced in the same sequencing run as the test sample is not used for the statistical distribution for the variant class A>C.

In some embodiments, at least 30 data points are included in the statistical distribution. The at least 30 data points may be from two or more samples in a single sequencing run. For data points less than 30, the true distribution may not be represented by the data points.

Figure 3A:
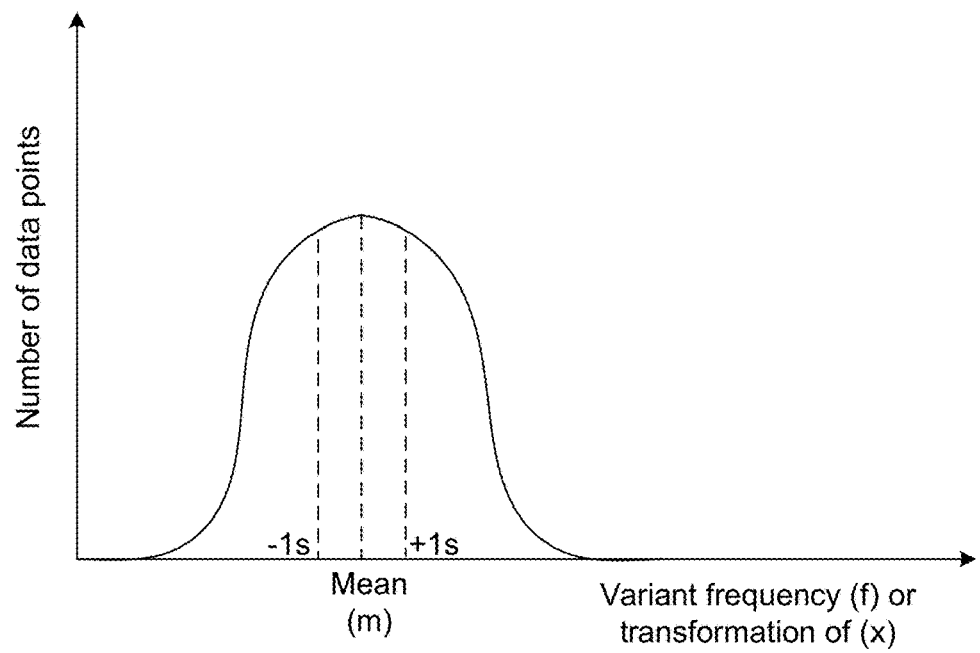
FIG. 3A illustrates an ideal statistical model of variant frequency distribution for variants in a variant class at each location of a plurality of locations in a target region in one or more samples according to embodiments of the present invention.

FIG. 3A illustrates an ideal statistical distribution (normal distribution) of variant frequency for variants of a same class. FIG. 3A is for illustration purpose only. Actual statistical distribution of variant frequency of a variant class may depend on the samples, and may be of other forms of distribution, such as a bi-modal distribution. In some embodiments, some forms of transformation, such as the square, square root, or logarithmic, of the variant frequency may form a distribution closer to a normal distribution.

In FIG. 3A, the x-axis represents the variant frequency value of a variant class, and y-axis represents the number of data points with a particular variant frequency value f. As shown in the ideal normal distribution in FIG. 3A, a mean value m and a standard deviation s may be determined based on the distribution.

Figure 3B:
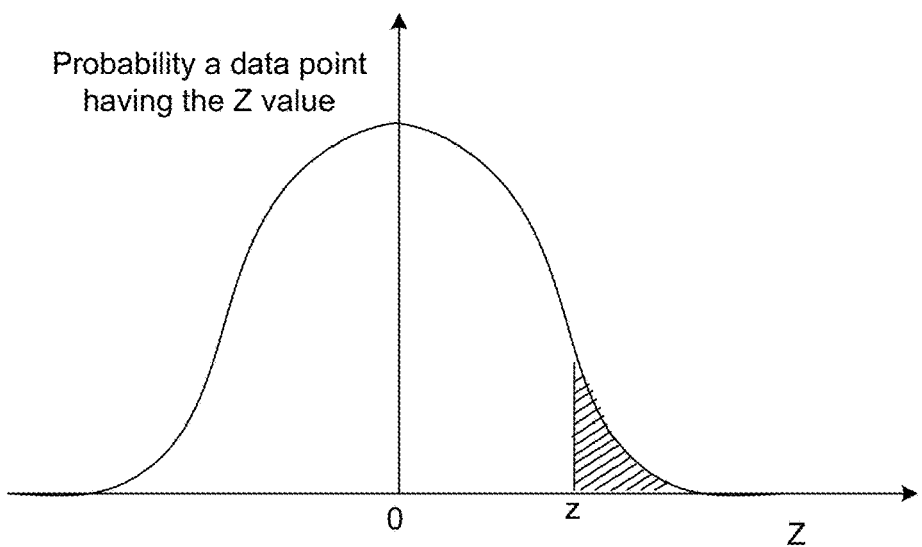
FIG. 3B illustrates the probability that the variant frequency of a variant at a specific location on a specific sample will have a given Z value according to embodiments of the present invention.

FIG. 3B illustrates a probability that the variant frequency of a variant at a specific location on a specific sample will have a given Z value, where the probability and the Z value can be derived from the statistical distribution shown in FIG. 3A. In some embodiments, FIG. 3B may be a normalized distribution of FIG. 3A based on the mean and the standard deviation. In some embodiments, more complicated transformation or conversion, such as logarithmic transformation, may be used. The shaded area in FIG. 3A indicates a cumulative probability for all Z values equal to or greater than z.

Figure 3C:
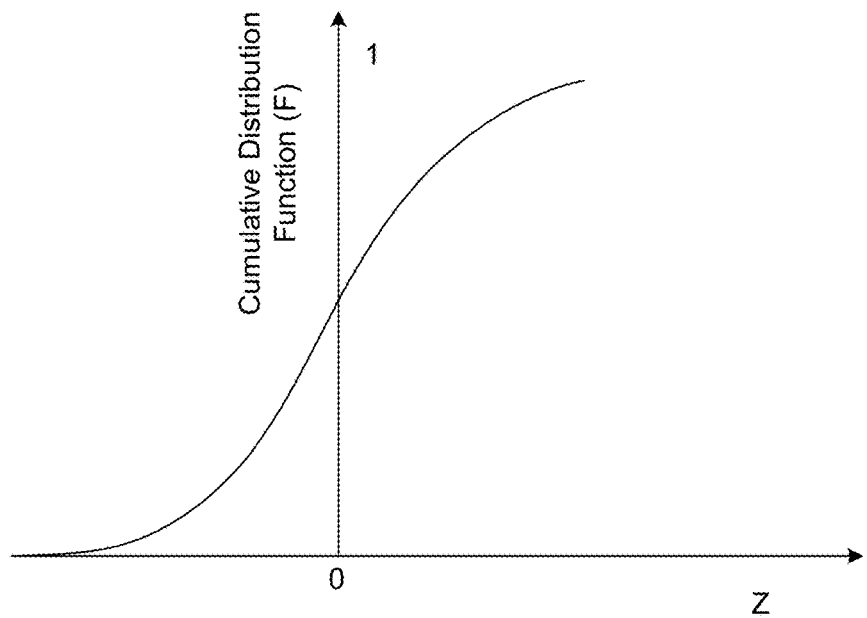
FIG. 3C shows the cumulative distribution function of the probability that a Z value takes on a value less than or equal to z according to embodiments of the present invention.

FIG. 3C shows a cumulative distribution function F of the probability that a Z value takes on a value less than or equal to z.

Figure 3D:
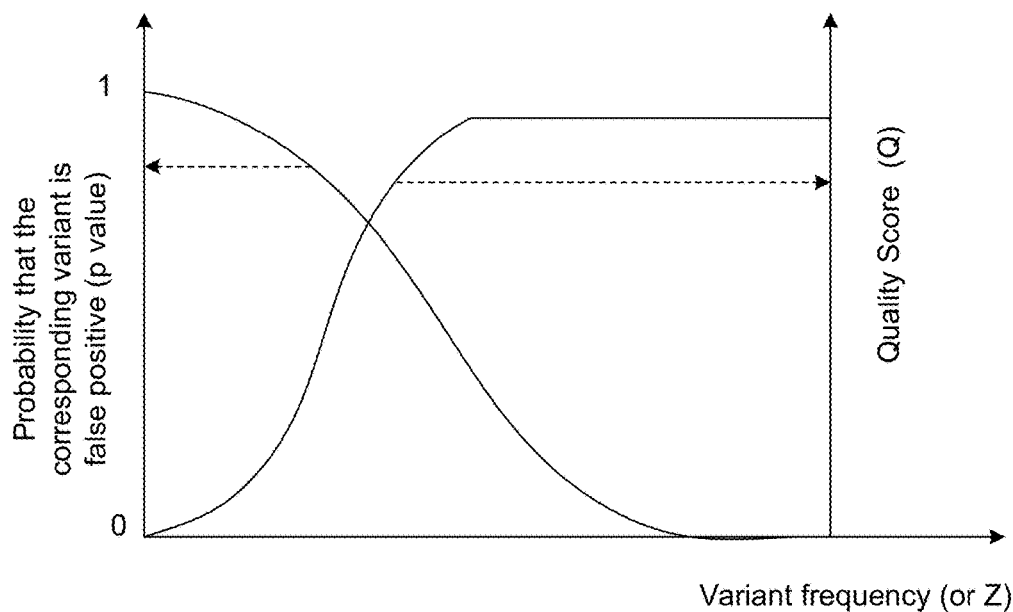
FIG. 3D shows the probability that a variant with a variant frequency value or Z value is a false positive, and the associated quality score for making a variant call according to embodiments of the present invention.

FIG. 3D shows a base-calling error probability (p-value) that a variant with a specific variant frequency value or Z value is a false positive on the primary axis on the left, and an associated quality score Q for making a variant call on the secondary axis on the right. In some embodiments, the p-value may be calculated by 1-F. In some embodiments, the quality score Q may be a Phred quality score given by $Q=-10 \log_{10} P$, or any variations of the Phred quality score.

B. Method of Statistical Model Based Variant Calling

Figure 4:
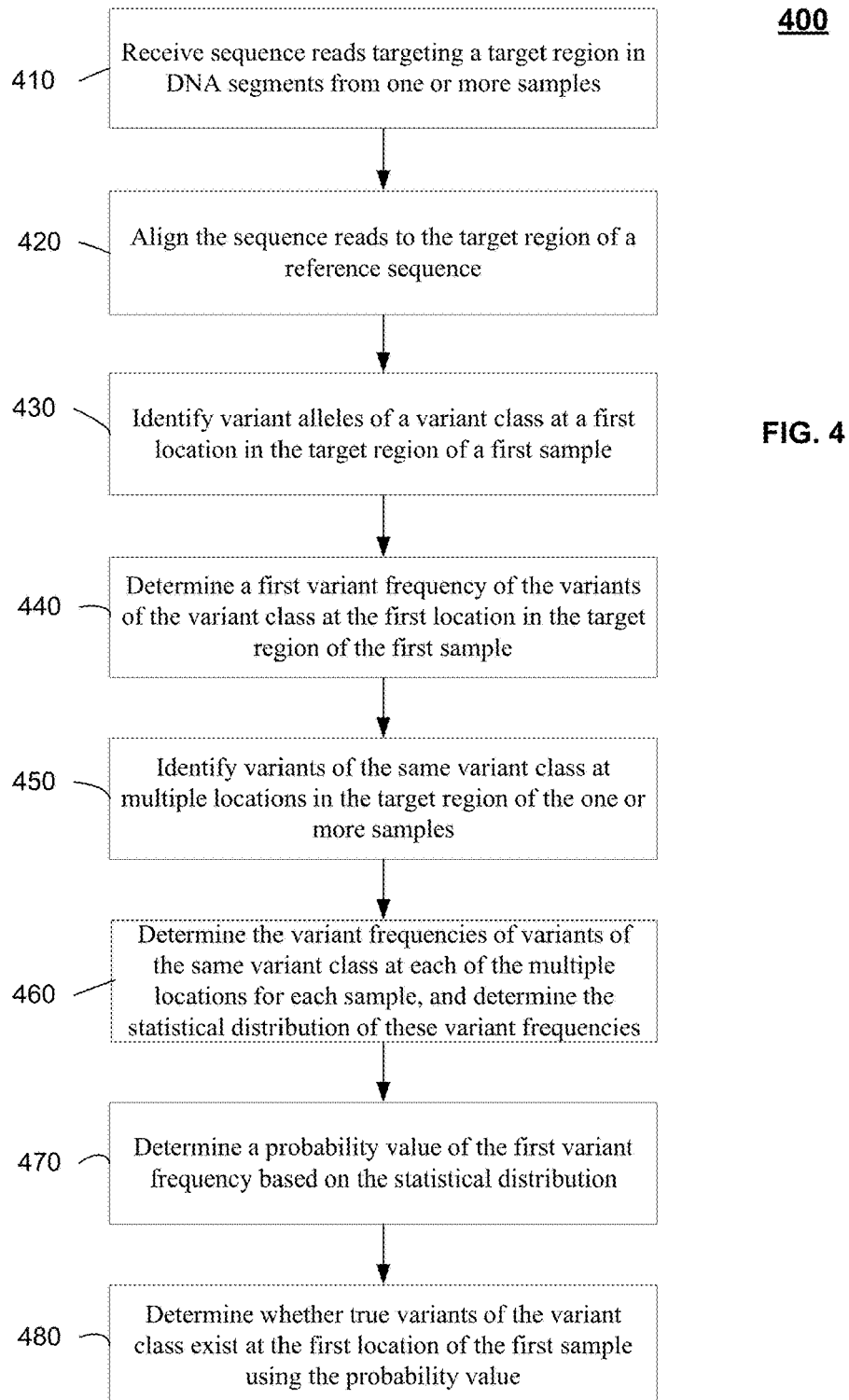
FIG. 4 is a flowchart illustrating a method of variant calling using statistical models according to embodiments of the present invention.

FIG. 4 illustrates a method 400 of variant calling using a statistical model. As with other methods, embodiments can include all or some of the procedures described, and some procedures may include additional procedures or sub-procedures.

At block 410, sequence reads targeting a target region in one or more samples in a single sequencing run are received. Sequence reads data may be received and stored in any format that can be read and parsed by a computer. In some embodiments, pre-processing of the sequence reads data may be performed to remove low-quality reads or adapter sequences. In some embodiments, barcodes or MIDs may be removed, and sequence reads from a same sample may be labeled or grouped.

At block 420, the sequence reads are aligned to a target region of a reference sequence, e.g., as described in block 170 of method 100.

At block 430, variant alleles of a same variant class at a specific sequence location on the aligned sequence reads of a test sample can be identified and counted to determine a variant count. The read count for the specific sequence location on the aligned sequence reads of the test sample can be determined as well. For example, as shown in FIG. 2, the total number of C at location 205 in the sequence reads of the test sample is the variant count for variant class A>C at location 205, and the total number of reads at location 205 in the sequence reads of the test sample is the read count for variant class A>C at location 205. In some embodiments, the read count of the specific location for the test sample may be determined in a separate procedure.

At block 440, the variant frequency of variants of the same class at the specific location is determined. In one embodiment, the variant frequency can be determined by dividing the variant count by the read count at the specific location in the test sample. In another embodiment, the variant frequency can be determined by dividing the variant count by a non-variant count (e.g., read count minus variant count) at the specific location in the test sample. One skilled in the art will appreciate the various types of forms of the variant frequency that can be used.

At block 450, for each sample sequenced in the same sequencing run as the test sample, variants of the same class, such as A>C, are identified and counted at each location of a plurality of locations where a reference allele of the variant class, for example A, exists on the reference sequence in the target region. Similarly, for each sample in the same sequencing run, the read count for each of the plurality of locations where the reference allele of the variant class is found on the reference sequence can be determined.

At block 460, for each sample sequenced in the same sequencing run as the test sample, variant frequency for variants of the same variant class, such as A>C, at each location of the plurality of locations may be determined by dividing the variant count for each location by the read count for that location. Thus, if, for example, 3 samples are sequenced together in a sequencing run, and 30 locations on the reference sequence in the target region have a reference allele for a variant class, up to 90 variant frequencies may be calculated, one for each location on each sample. These variant frequencies can be used to determine a statistical distribution of variant frequencies for variants of the same class in the same sequencing run. Note that variant frequencies of other variant classes are not included for determining the statistical distribution. In addition, data points obtained from other sequencing runs may not be included for determining the statistical distribution, in order to reduce the effect of variations between sequencing runs that may affect the accuracy of the distribution model.

At block 470, a probability value corresponding to the variant frequency for variants of the same class at the specific location in the test sample is determined by comparing the variant frequency to parameters of the statistical distribution formed at block 460. In some embodiments, the probability value may be an actual probability, an accumulative distribution, or a quality score. In same embodiments, the parameters of the statistical distribution may be one or more of a mean value and a standard deviation.

At block 480, a variant call is made based on the probability value and a threshold value to determine whether variants of the variant class at the specific location on the test sample are true positives. In some embodiments, the threshold value may be a single value. In some embodiments, the threshold value may be a function of, for example, the variant frequency. In some embodiments, the threshold value may be determined using a machine learning algorithm, such as support vector machines (SVM), based on a training data set. In some embodiments, the threshold value may be determined based on training data obtained from different sequencing runs.

The method described above may be better understood in light of the examples below.

C. Examples

The examples given below illustrate the method described above in this section. In the examples, models based on a statistical distribution of logarithmic variant frequency for a variant class are used because the variant frequencies are not in normal distribution, while the distribution of the logarithmic variant frequencies is close to normal as explained below.

Table 2 shows the results of normality tests, such as Lilliefors test and Shapiro-Wilk test, applied to both original variant frequency f and its logarithmic transformation x for a wild type data with false positives of Exon 20 substitution T790M (C>T at 2369) and Exon 21 substitution L858R (T>G at 2573). The results show that x has larger probability of obtaining the observed sample results (P-values) (>0.08) when the normal distribution assumption is used, which indicates a smaller discrepancy between the actual distribution and the normal distribution, and f has smaller P-values (<0.016). Therefore, x is closer to the normal distribution than f.

TABLE 2

P-values of Normality Tests for f and x

| False Positive | Variable | P-value of Lilliefors test | P-value of Shapiro-Wilk test |
|---|---|---|---|
| T790M | f | 0.008805 | 0.001830 |
| | $\log_{10}(f + 1e-06)$ | 0.348639 | 0.084104 |
| L858R | f | 0.014024 | 0.015862 |
| | $\log_{10}(f + 1e-06)$ | 0.602277 | 0.520155 |

Thus, in order to use the normal approximation to make a statistical analysis, a logarithmic transformation of variant frequency is made first because the transformed variant frequency is closer to normal distribution than the original variant frequency for most noises. In some embodiments, in order to avoid negative infinity values when f=0, the following logarithmic transformation is used $$x = \log_{10}(f+e),$$

where e is an adjustment constant for avoiding negative infinity values. The adjustment constant e can be set to any appropriate value. For example, in some embodiments, e can be set to $10^{-6}$, thus the minimum x value is −6.

After the logarithmic transformation, mean value m and standard deviation s of the normal distribution approximation can be calculated. The normal distribution approximation can then be used to calculate a probability value of the detected variants at a sequence location. For example, for an observed variant in the variant class at a location with a variant frequency of f1, and a logarithmic variant frequency of $x1=\log_{10}(f1+e)$, with sufficient depth (total read count), a statistical probability value z-score can be calculated by $$z=(x1-m)/(s/\text{sqrt}(n)),$$

where n is the number of reference data points used in estimating s and m. Calculation results indicate that the z score is large for large n, which may generate very small base-calling error probability (p value), and hence very large quality score. Therefore, in some embodiments, z-core is replaced by z-like score, which is calculated by replacing n in the above equation with min(n, N). N can be set to any appropriate value, In some embodiments, N is set to 36. In some embodiments, a lower bound s2 can also be set for s/sqrt(min(n, N)) in situations where s is too small. s2 can be set to any appropriate value, such as, for example, a default value of 0.01. Thus, in some embodiments, the z-like score can be expressed as $$z'=(x1-m)/\max(s2,s/\text{sqrt}(\min(n,N))).$$

Using the z-score or z-like score z', base-calling error probability p value can be determined by p=1−F(z) or p=1−F(z'), where F is the cumulative distribution function of the standard normal distribution. The variant calling quality score $Q_{AMP}$ can then be determined using the Phred score. In some embodiments, $Q_{AMP}$ can be defined as a Phred-like score:

$$Q_{AMP}=-10 \log_{10}(\max(p,\text{minP})),$$

where $\text{minP}=10^{-maxQ/10}$. maxQ can be set to any suitable value. For example, in some embodiments, maxQ may be set to 80 or 130.

In some embodiments, robust estimations of central position and variation of data, instead of sample mean and sample standard deviation, can be used to calculate the quality scores.

In some embodiments, a classification method, such as the support vector machines (SVM) with linear kernel, can be used to separate true positives from false positives, using a training data set with known true positives and false positives. In some embodiments, a threshold value may be set by visualizing the data.

Figure 5:
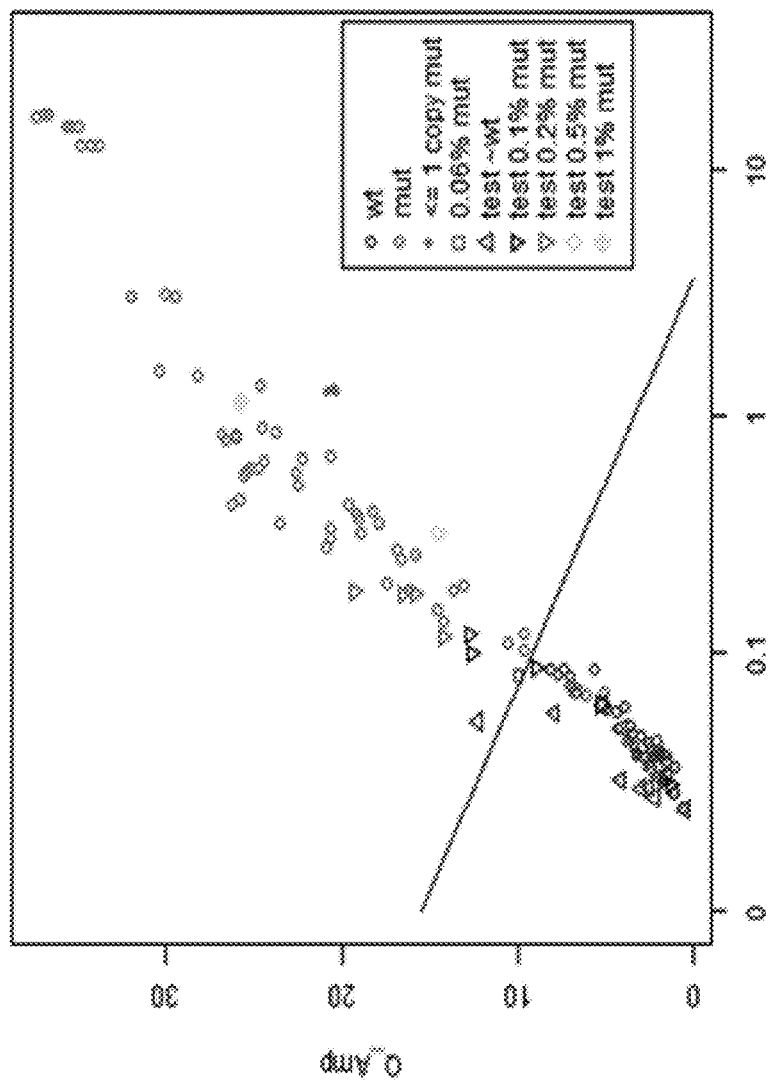
FIG. 5 illustrates variant quality scores $Q_{AMP}$ determined using a statistical model for training data and test data of EGFR T790M of exon 20 with a separator line determined by support vector machines (SVM) according to embodiments of the present invention.
Figure 6:
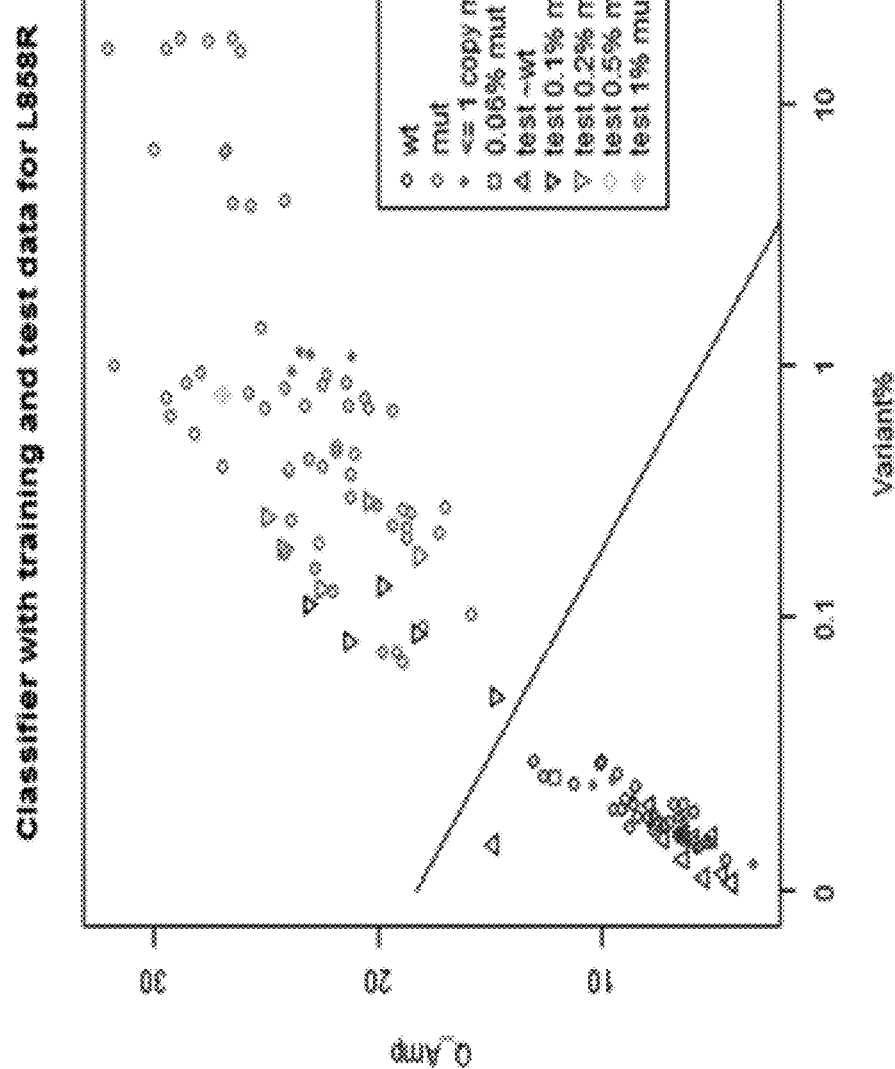
FIG. 6 illustrates variant quality scores $Q_{AMP}$ determined using a statistical model for training data and test data of EGFR L858R of exon 21 with a separator line determined by SVM according to embodiments of the present invention.

FIGS. 5 and 6 show example results of the above method applied to sequence read data from real samples. FIG. 5 shows variant calling quality score $Q_{AMP}$ with maxN=4 for different training data and test data of EGFR T790M of exon 20 (C>T at 2369) with a separator line determined by SVM. FIG. 5 shows that the variants and wild type data are not well separated, and thus it may be difficult to distinguish true mutations and false positives with variant frequencies of 0.1% or less. However, for all test data with variant frequencies of 0.5% or more, and most test data with variant frequencies of at least 0.2%, true positives and false positives can be correctly distinguished.

FIG. 6. shows variant calling quality score $Q_{AMP}$ with maxN=4 for different training data and test data of EGFR L858R of exon 21 (T>G at 2573) with a separator line determined by SVM. FIG. 6 shows that all testing data, including those with variant frequencies of 0.1%, can be classified correctly.

IV. Variant Calling for Specific Variant at a Specific Location Using a Comparison With One or More Reference Samples In some embodiments of this invention, variants and wild type counts of a variant at a same location in different samples can be compared to make variant call. This method is especially useful if wild type (usually normal) samples are available as negative control in a sequencing run.

A. Method of Comparing Test Samples With Reference Samples for Detecting a Specific Variant at a Specific Location This method can be used to compare a specific variant at a specific location for different samples, and can be applied to as low as two data points.

Figure 7:
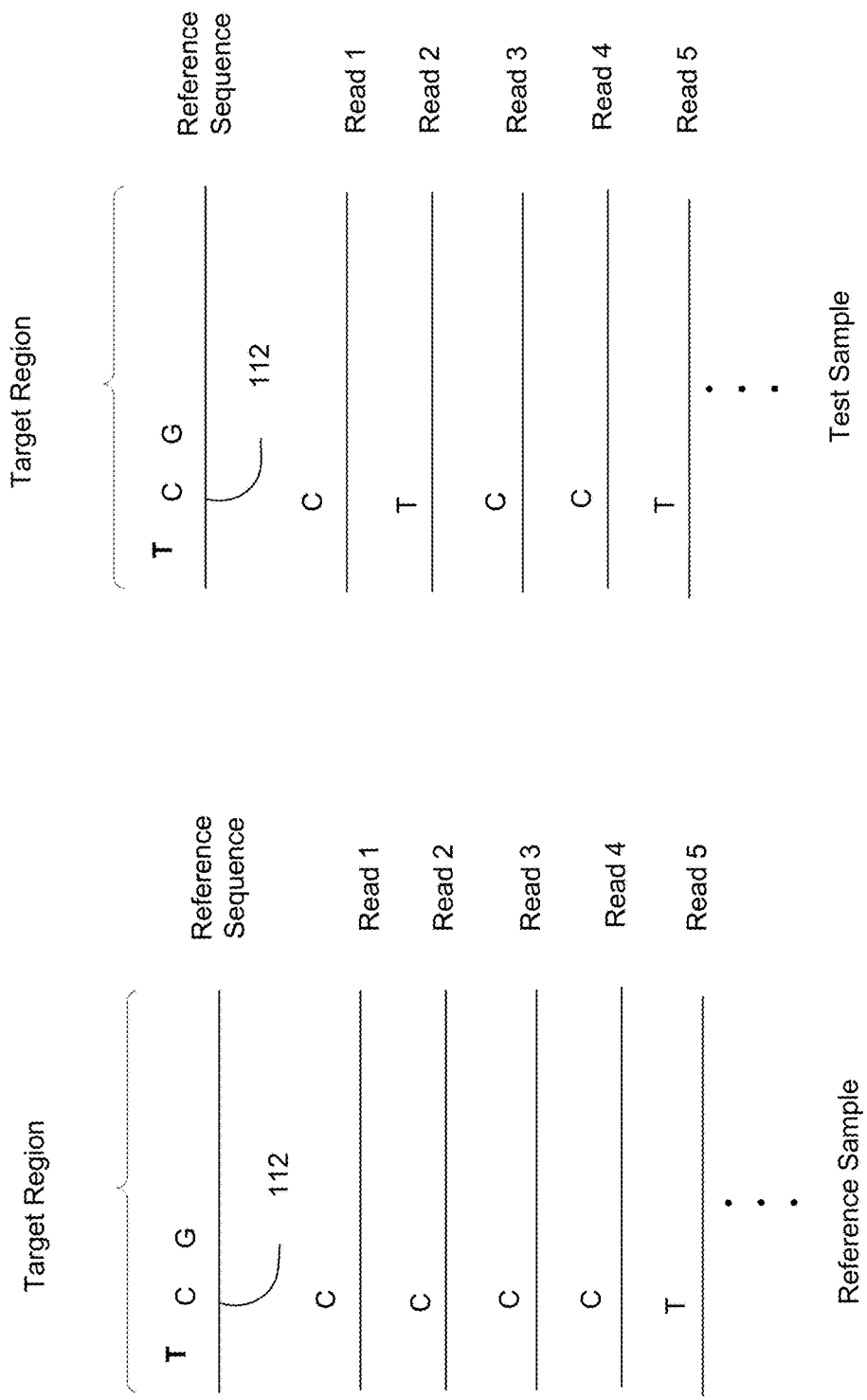
FIG. 7 illustrates a specific variant at a specific genomic location on sequence reads of a reference sample and a test sample according to embodiments of the present invention.

FIG. 7 illustrates a specific variant C>T at a specific location 112 on sequence reads of a reference sample and a test sample. As shown in FIG. 7, the reference allele at location 112 of the reference sequence is C, and sequence reads at location 112 for the reference sample are mostly Cs, but may have variants of C>T caused by sequencing errors. For the test sample, the sequence reads at location 112 may also be Cs due to low variant frequency, some Ts due to true mutations, and some Ts due to sequencing errors.

The reference sample is theoretically without true mutations, but sequencing errors may cause small variant count as shown in FIG. 7. The variant counts of the reference sample and the test sample, and the wild type counts of the reference sample and the test sample for a specific variant at a specific location can be determined based on the sequence reads, and put into a table as shown in Table 3 below. The count data for the test sample and the reference sample can be used for determining whether the variant frequency of the test sample is significantly larger than the variant frequency of the reference sample at the same location.

In Table 3, a1 is the count of a specific variant at a specific location in the reference sample, n1 is the depth of the sequence reads for the reference sample, and w1=n1−a1 represents the wild type count at the specific location in the reference sample. a2, n2 and w2 are the corresponding variant count, depth and wild type count for the test sample. Table 3 also lists row sums a=a1+a2, w=w1+w2, and total counts n=n1+n2.

TABLE 3

Count table for a reference sample and a test sample

| Count Table | Reference Sample | Test Sample | RowSum |
|---|---|---|---|
| Variant Count | a1 | a2 | a |
| Wild Type Count | w1 | w2 | w |
| Total Count (Depth) | n1 | n2 | n |

There are a number of ways to test whether (a1, w1) and (a2, w2) are significantly different in ratio. In some embodiments, because n1 and n2 can be very large in ultra-deep sequencing, one-sided chi-squared test is preferably used. In the one-sided chi-squared test, proportions f1=a1/n1 and f2=a2/n2 are calculated first. If f2<=f1, that is, the proportion for test sample is not higher than the proportion for the reference sample (which is known to be a false positive), a very small quality score, such as 2, which corresponds to an error rate p=0.63, can be set, and there is no need for further analysis. However, if f2>f1, chi-squared statistic can be calculated as $$\chi^2=n\times(a1\times w2-a2\times w1)^2/(n1\times n2\times a\times w).$$

A one-sided variant calling error probability p-value can be calculated as $p=0.5\times(1-\text{pchisq}(\chi^2, d))$, where pchisq is the chi-squared cumulative distribution function with a degree of freedom of d. In some embodiments, the degree of freedom d is 1.

Another method to test whether (a1, w1) and (a2, w2) are significantly different in ratio is the Pearson proportion test for large samples. In Pearson proportion test, two proportions, p1_hat=a1/n1 and p2_hat=a2/n2, are calculated first. A Z-score can then be determined by $$Z=(p2\_hat-p1\_hat)/\text{sqrt}(V),$$

where V may be calculated with at least one of the following two formulae:

$$V=p1\_hat\times(1-p1\_hat)/n1+p2\_hat\times(1-p2\_hat)/n2, \text{ and}$$

$$V=p\_hat\times(1-p\_hat)\times((1/n1)+(1/n2)),$$

where p_hat=(a1+a2)/(n1+n2). A one-sided p-value can then be calculated as $p=1-p_{norm}(Z)$, where $p_{norm}$ is n is the cumulative probability distribution function.

In some embodiments, Fisher's exact test may be used to determine whether (a1, w1) and (a2, w2) are significantly different in ratio. Fisher's exact test uses hypogeometric distribution. The computation for Fisher's exact test may be more complicated and may cause overflow for large samples.

After the p-value is calculated, the corresponding quality score can be defined as $Q_{LOC}=-10\times\log_{10}(p)$. Note that in the one-sided chi-squared test, p is in the range of (0, 0.5). In some embodiments, to avoid the difficulty of numerical computation when p is close to 0, $Q_{LOC}=-10\times\log_{10}(\max(p, \min P))$ is used, where minP can be set to any suitable value, such as $10^{-13}$, which is equivalent to setting maximum quality score to 130.

B. Method of Selecting Reference Samples for Detecting a Specific Variant at a Specific Location Various methods can be used to set the reference counts for a specific variant at a specific location in a sequencing run of multiple samples. One method is to use the sum of the variant counts and the sum of the depths of two samples in the same sequencing run with the lowest variant frequencies for the specific variant at the specific location and having depths of no less than a minimum value minD. In some embodiments, the minD may be set to 3000. In some embodiments, to avoid the rare possibility that all samples have high variant frequencies for a specific variant at a specific location, when the reference proportion is greater than f0 (which may be set to, for example, 0.01 or 1%), a1 is set to f0×n1. Thus, the a1 value used is either the actual a1 value or f0×n1, whichever is smaller. With this method, if wild type samples are contaminated with variants, the wild type samples with variant contamination will show high variant frequency, and hence will not be selected as reference samples for the particular variant; thus, quality score $Q_{LOC}$ of other samples are usually not affected. Some complex mutations consist of multiple simple mutations. In such situations, $Q_{LOC}$ can be defined as the median value of the quality scores $Q_{LOC}$ of all simple mutation components of the complex mutation.

Known wild type sample can also be used as a reference sample. However, if wild type samples are contaminated with variants, quality scores $Q_{LOC}$ of other samples may be low.

Figure 8:
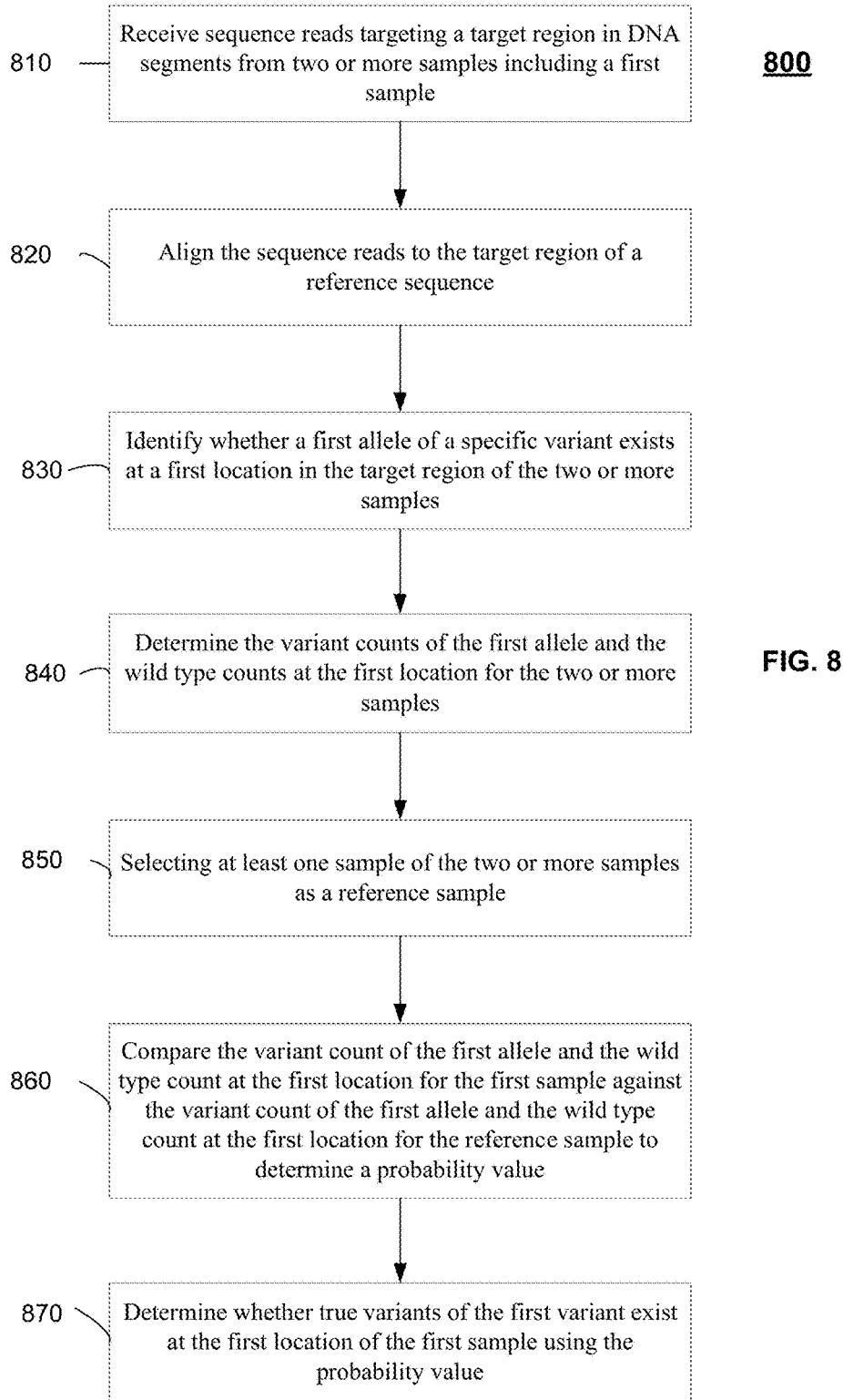
FIG. 8 is a flowchart illustrating variant calling for a specific variant at a specific sequence location by comparing sequence reads data of a test sample and a reference sample according to embodiments of the present invention.

C. Data Analysis by Comparing Test Samples with Reference Samples to Detect a Specific Variant at a Specific Location FIG. 8 illustrates a method 800 of variant calling by comparing test samples with one or more reference samples to classify a specific variant at a specific location. As with other methods, embodiments can include all or some of the procedures described, and some procedures may include additional procedures or sub-procedures.

At block 810, sequence reads targeting a target region in DNA segments from one or more samples in a single sequencing run are received. Sequence reads data may be received and stored in any format that can be read and parsed by a computer. In some embodiments, pre-processing of the sequence reads data may be performed to remove low-quality reads or adapter sequences. In some embodiments, barcodes or MIDs may be removed, and sequence reads from a same sample may be labeled or grouped.

At block 820, the sequence reads are aligned to a target region of a reference sequence as described in block 170 of method 100.

At block 830, variant alleles for a specific variant at a specific sequence location on the aligned sequence reads can be identified for all samples by comparing the aligned sequence reads against the reference sequence. Any suitable alignment technique may be used, as will be known by one skilled in the art.

At block 840, variant counts and read counts for the specific variant at the specific sequence location for all samples can be determined. The variant count is the the total number of same variant alleles, such as Cs for A>C variants, at a specific location on different sequence reads of a sample. The read count is the total number of reads of the specific location for a sample.

At block 850, at least one sample is selected as a reference sample. As described above, in some embodiments, a known wild type sample can be used as the reference sample. In some embodiments, two samples with the lowest variant frequencies in a sequence run can be used as the reference samples. In such embodiments, the sum of variant counts and the sum of the read counts of the two samples with the lowest variant frequencies can be used as the variant count a1 and the read count n1 for the reference sample in the calculation.

At block 860, variant counts and read counts for the specific variant at the specific sequence location for a test sample and the reference sample are compared to determine a probability value using methods such as the ones described above in Section IV(A). The probability value may be one or more of a chi-squared value, a cumulative probability distribution value, a p-value, a Z-value, and a quality score.

At block 870, a variant call is made based on the probability value and a threshold value to determine whether the specific variants at the specific location on the test sample are true positives. In some embodiments, the threshold value may be a single value. In some embodiments, the threshold value may be a function of, for example, the variant frequency. In some embodiments, the threshold value may be determined using a machine learning algorithm, such as support vector machines (SVM), based on a training data set. In some embodiments, the threshold value may be determined based on training data obtained from different sequencing runs.

D. Examples

The examples below show the results of variant calling by comparing test samples with reference samples for detecting a specific variant at a specific location.

Figure 9:
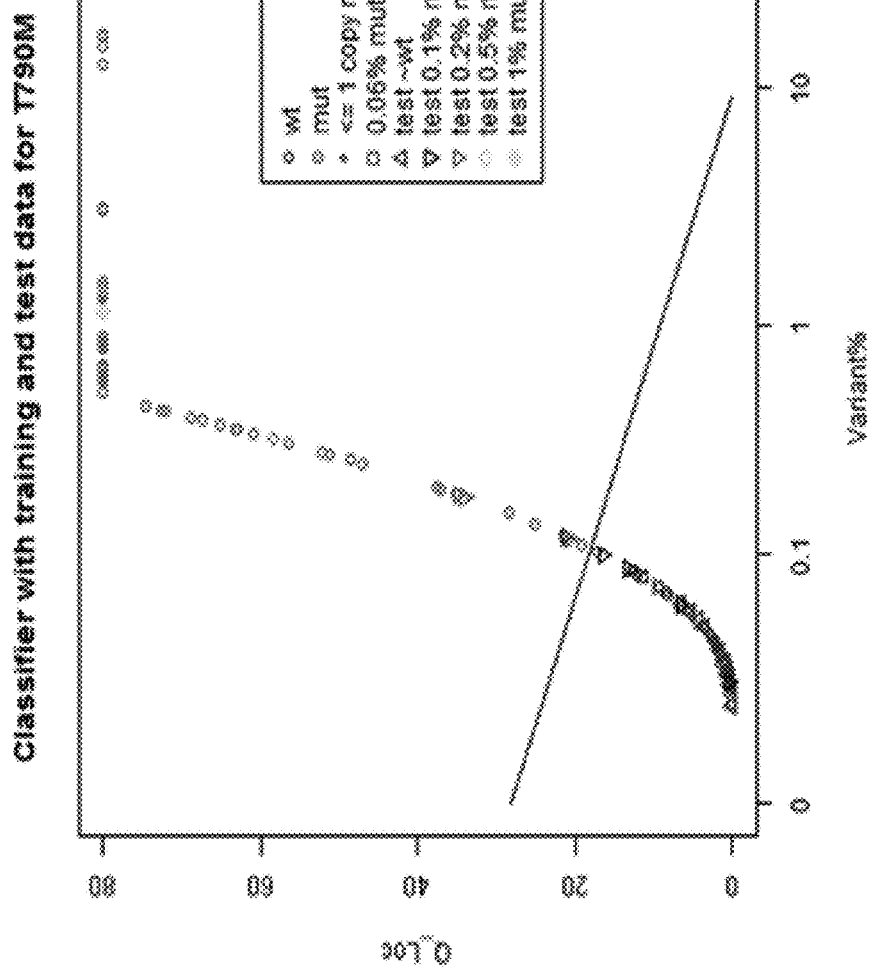
FIG. 9 illustrates localized variant quality scores $Q_{LOC}$ determined by comparing two samples for training data and test data of EGFR T790M of exon 20 with a separator line determined by SVM according to embodiments of the present invention.

FIG. 9 shows localized variant calling quality score $Q_{LOC}$ for training data and test data of EGFR T790M of exon 20 with a separator line determined by SVM. It can be seen from FIG. 9 that there is no misclassification of the wild type testing data even if the separator determined by SVM is lowered to call 0.1% of T790M as a true positive. In addition, a single threshold value of, for example, f>=0.1% or $Q_{LOC}$>=18, can be a good decision point for the T790M variant.

Figure 10:
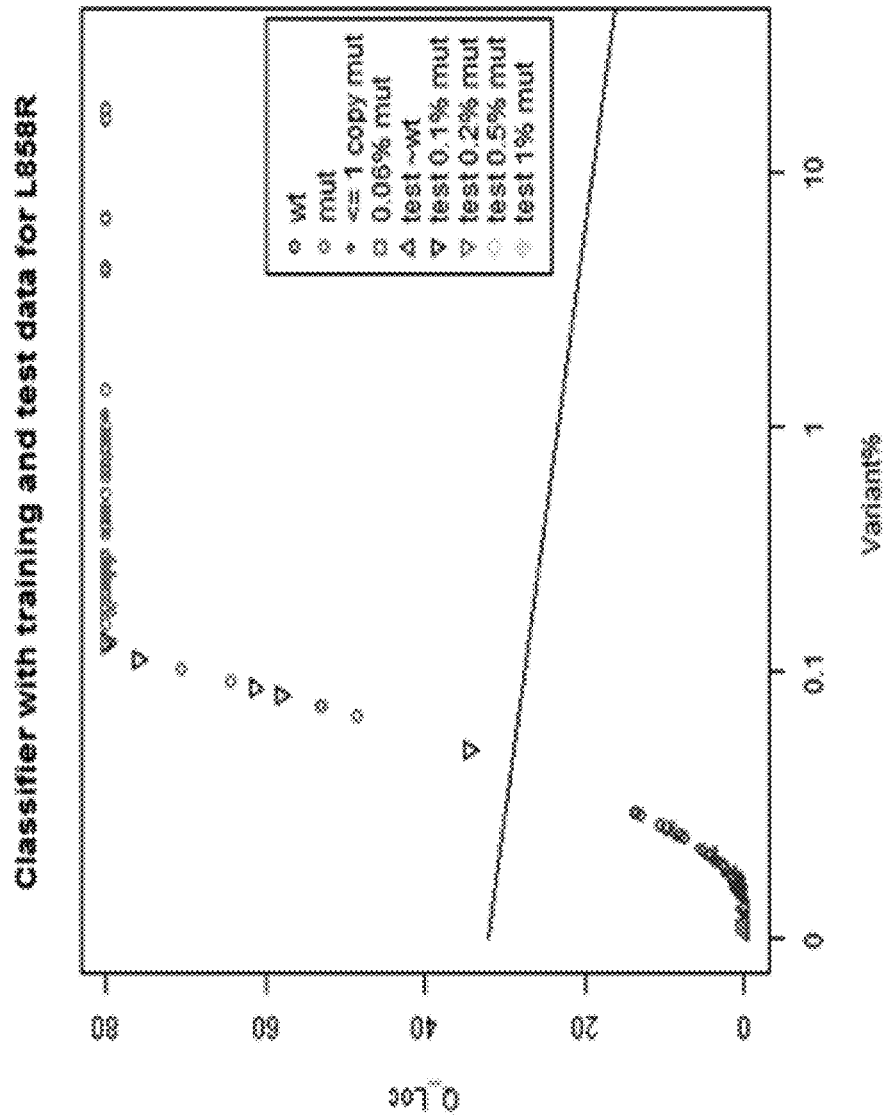
FIG. 10 illustrates localized variant quality scores $Q_{LOC}$ determined by comparing two samples for training data and test data of EGFR L858R of exon 21 with a separator line determined by SVM according to embodiments of the present invention.

FIG. 10 shows localized variant calling quality score $Q_{LOC}$ for training data and test data of EGFR L858R of exon 21 with a separator line determined by SVM. It can be seen that all testing data, including those with variant frequencies of 0.1%, are classified correctly. In addition, a single threshold value of, for example, $Q_{LOC}$>=18 can be a good decision point for the L858R variant.

Figure 11:
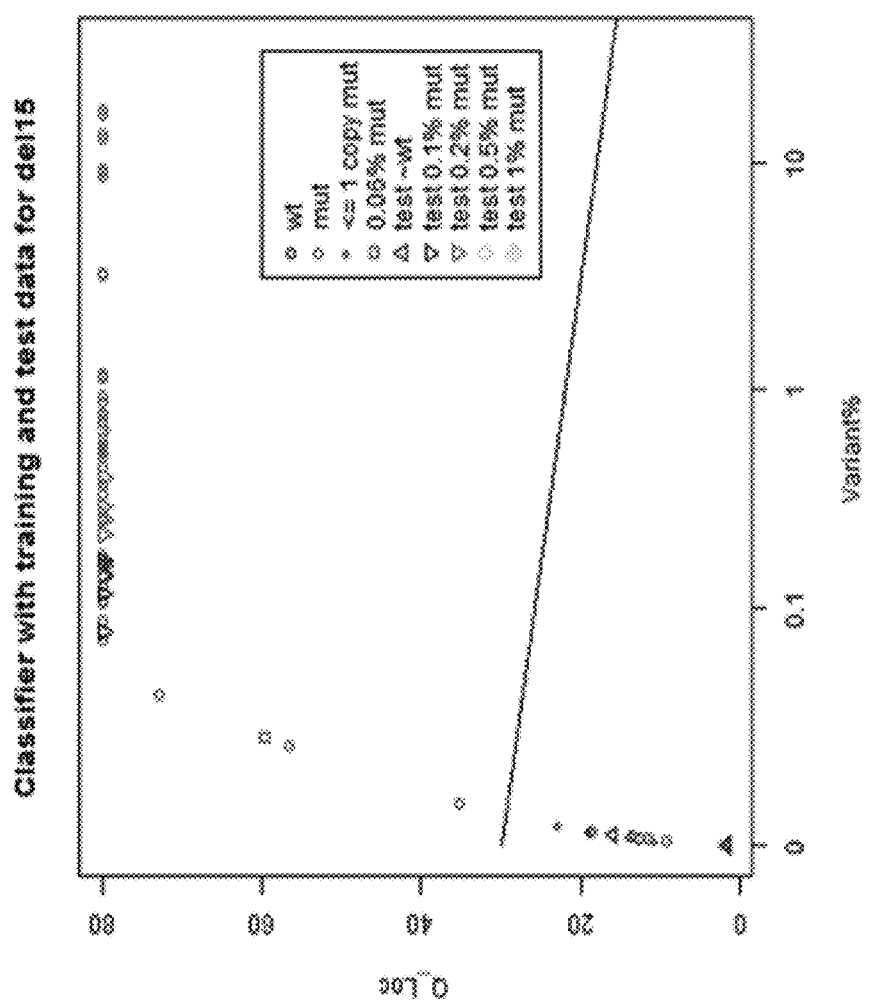
FIG. 11 illustrates localized variant quality scores $Q_{LOC}$ determined by comparing two samples for training data and test data of EGFR 15-base deletion 2235_2249del15 of exon 19 with a separator line determined by SVM according to embodiments of the present invention.

FIG. 11 shows localized variant calling quality score $Q_{LOC}$ for training data and test data of EGFR 15-base deletion 2235_2249del15 of exon 19 with a separator line determined by SVM. It can be seen that all testing data, including those with variant frequencies of 0.1%, are classified correctly. A single threshold value of, for example, $Q_{LOC}$>=18 or 20 can be set without using SVM to separate false positives from true positives.

FIGS. 9-11 also show that the localized variant calling score $Q_{LOC}$ has wider margin between the true positives and the false positives than the model based variant calling score $Q_{AMP}$.

V. Simplified Quality Score Estimation

In some applications, it may be time consuming to directly calculate p-value and quality score for every variant. Since quality scores only need to be reported as an integer, in some embodiments, the value of $Q_{LOC}$ and $Q_{AMP}$ can be discretized. For example, when f2<=f1, the quality score can be set to 2; when f2>f1, the quality score can be set to 3, 4, ..., or maxQ, which may be set to, for example, 130 in some embodiments.

In some embodiments, the quality score can be determined using, for example, $\chi^2$ values $q_{chisq}$ or normal quantile value $q_{norm}$, and a look-up table as shown in FIG. 12. In FIG. 12, $\chi^2$ values and $q_{norm}$ values for Q=3.5, 4.5, ..., 129.5 are calculated and provided in a look-up table. Thus, a searching algorithm, such as a binary search algorithm, can be used to determine the best approximate integer value of Q in 3, 4, ..., 130 based on the $\chi^2$ value or the $q_{norm}$ value.

VI. Sample Amount Required to Avoid Zero Events

One practical issue for blood test is to determine the amount of gDNA sufficient for detecting the variants such that low frequency mutations can be detected. In some embodiments of this invention, probability of zero events detection can be used to estimate the required sample amount.

Based on the Avogadro constant of $6.022 \times 10^{23}$/mol, the average molecular weight of 650 Daltons (g/mol) per base pair, and $3.096 \times 10^9$ base pairs per human genome, it can be calculated that 1 nanogram (ng) of human gDNA contains $6.022 \times 10^{23}/(650 \times 3.096 \times 10^9 \times 10^9) = 300$ molecules.

The amount of gDNA needed for detecting a mutation depends on the mutation frequency, and can be determined by solving the statistical problem of avoiding zero events. See, e.g., Lachin, Biostatistical Methods: The Assessment of Relative Risks, p. 19, Wiley (2000). Assume that the number of mutant copies in a blood sample is B, and the total number of DNA copies is N, the mutant probability is p=B/N. According to the binomial distribution, the probability of not obtaining the mutant copy in a random trial is (1−p), and the probability of not getting a mutant copy in N random trials is $(1-p)^N$. Therefore, the following inequality can be set $$(1-p)^N <= \alpha,$$

where α is the maximum allowed probability that no mutation will be detected (maximum allowed failing rate), and 1−α is the upper confidence limit. Thus, sample size N can be estimated by solving the inequality as $$N >= \ln(\alpha)/\ln(1-p)$$

For rare mutations where p<<1, the estimation can be simplified using Taylor expansion $$\ln(1-n) \approx -p,$$

and the sample size estimation becomes $$N >= -\ln(a)/p.$$

Since −ln(0.05)=2.9957, and −ln(0.005)=5.2983, 3/p or 5.3/p may be used to estimate the sample size N for rare mutations with upper confidence limits of 0.95 and 0.995, respectively.

Table 4 lists the estimated number of gDNA molecules required to include at least one mutant copy with maximum allowed failing rates α of 0.05 and 0.005. For example, to detect 0.1% (p=0.001) mutation with 95% upper confidence level (α=0.05) of getting at least one mutant copy in the sample, 2995 gDNA copies are needed, which are equivalent to about 10 ng of gDNA molecules.

TABLE 4

Estimation of copy number and weight of gDNA molecules for rare mutation detection

| | α = 0.05 | | α = 0.005 | |
| --- | --- | --- | --- | --- |
| p | copy# | ng | copy# | ng |
| 0.01 | 300 | 1.0 | 530 | 1.8 |
| 0.005 | 600 | 2.0 | 1060 | 3.5 |
| 0.002 | 1500 | 5.0 | 2650 | 8.8 |
| 0.001 | 2995 | 10.0 | 5300 | 17.7 |

VII. Application and Verification

The methods described above in Sections III and IV can help to determine the threshold of variant frequencies used as decision criteria. The methods can successfully detect substitutions with frequencies of 0.1-0.3% with sufficient input DNA amount. Since the false positive rate depends on mutation context and location, for certain substitutions at certain locations, variants with variant frequencies of as low as 0.03% can be correctly detected.

For moderate size insertions, deletions and complex mutations, such as a 15-base deletion, it is difficult to generate these type of mutations randomly in sequencing, and the main source of errors is the carry-over contamination from other samples. Thus, with well-established washing protocol between runs, variants of these types with variant frequencies of as low as 0.0025% can be correctly detected.

Illumina MiSeq Reporter (MSR) can be used in a non-standard way to verify the low frequency variants detected by the methods described in this disclosure. MSR uses a somatic variant caller with a built-in Poisson model to report low-frequency variants. The lowest frequency that MSR reports is depth dependent. Based on the Poisson model, the lowest variant counts and frequencies that MSR somatic variant caller reports can be calculated and set as default settings as shown in Table 1. For example, when the depth is 100, the lowest reported frequency is 5%; when the depth is 5000, the lowest reported frequency is 1.36%; when the depth gets even higher, the lowest reported frequency becomes close to but above 1%.

In some embodiments, MSR using a sample containing known variants as a reference sample can be run such that MSR would report a wild type allele as a "variant allele" of the reference sample, and report an actual variant allele as a "wild type allele". In this way, variant calls using methods described in this disclosure can be verified. This nonstandard usage of MSR may have several drawbacks. First, it may only be used to verify known variants. Second, the variant calling quality score that MSR reports is for the wild type rather than the actual variant. Third, when there are multiple overlapping known variants, it becomes tedious or difficult to use this method. However, MSR can be used as a verification tool for known variants after the above drawbacks are considered. It is especially useful for moderate size indels that MSR mapping/alignment software may report as unmapped reads when the whole genome is used as the reference sequence.

VIII. Computer System and Sequencing System

Figure 13:
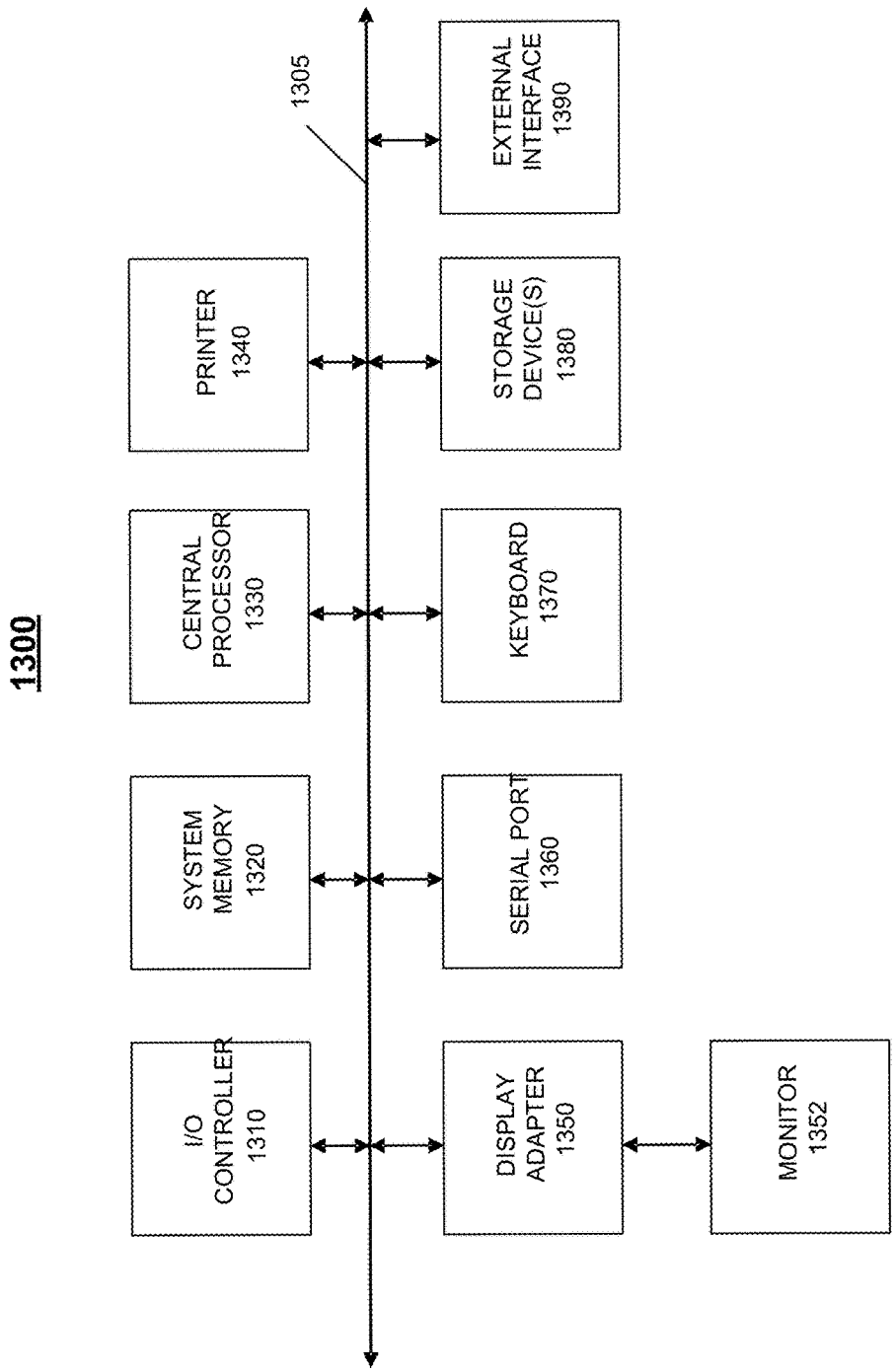
FIG. 13 shows a block diagram of an example computer system for low frequency variant calling according to embodiments of the present invention.

Any of the computer systems mentioned herein may utilize any suitable number of subsystems. Examples of such subsystems are shown in FIG. 13 in computer apparatus 1300. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 13 are interconnected via a system bus 1305. Additional subsystems such as a printer 1340, keyboard 1370, storage device(s) 1380, monitor 1352, which is coupled to display adapter 1350, and others are shown. Peripherals and input/output (I/O) devices, which couple to I/O controller 1310, can be connected to the computer system by any number of means known in the art, such as serial port 1360. For example, serial port 1360 or external interface 1390 (e.g. Ethernet, Wi-Fi, etc.) can be used to connect computer system 1300 to a wide area network such as the Internet, a mouse input device, or a scanner. The interconnection via system bus 1305 allows the central processor 1330 to communicate with each subsystem and to control the execution of instructions from system memory 1320 or the storage device(s) 1380 (e.g., a fixed disk), as well as the exchange of information between subsystems. The system memory 1320 and/or the storage device(s) 1380 may embody a computer readable medium. Any of the values mentioned herein can be output from one component to another component and can be output to the user.

A computer system can include a plurality of the same components or subsystems, e.g., connected together by external interface 1390 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

In certain aspects, the invention also provides sequencing systems. An exemplary sequencing system is displayed in FIG. 14. The system depicted in FIG. 14 comprises a sequencing analysis module which may be located in a sequencing device and an intelligence module which is part of the computer system. The data sets (sequencing data sets) are transferred from the analysis module to the intelligence module or vice versa via a network connection or a direct connection. The data sets may for example be processed according to the flowchart as depicted on FIG. 4 or 8. The steps provided in the flowchart may conveniently be implemented by software stored on the hardware of a computer system for example according to the flowcharts as depicted in FIGS. 15A and 15B.

Figure 15A:
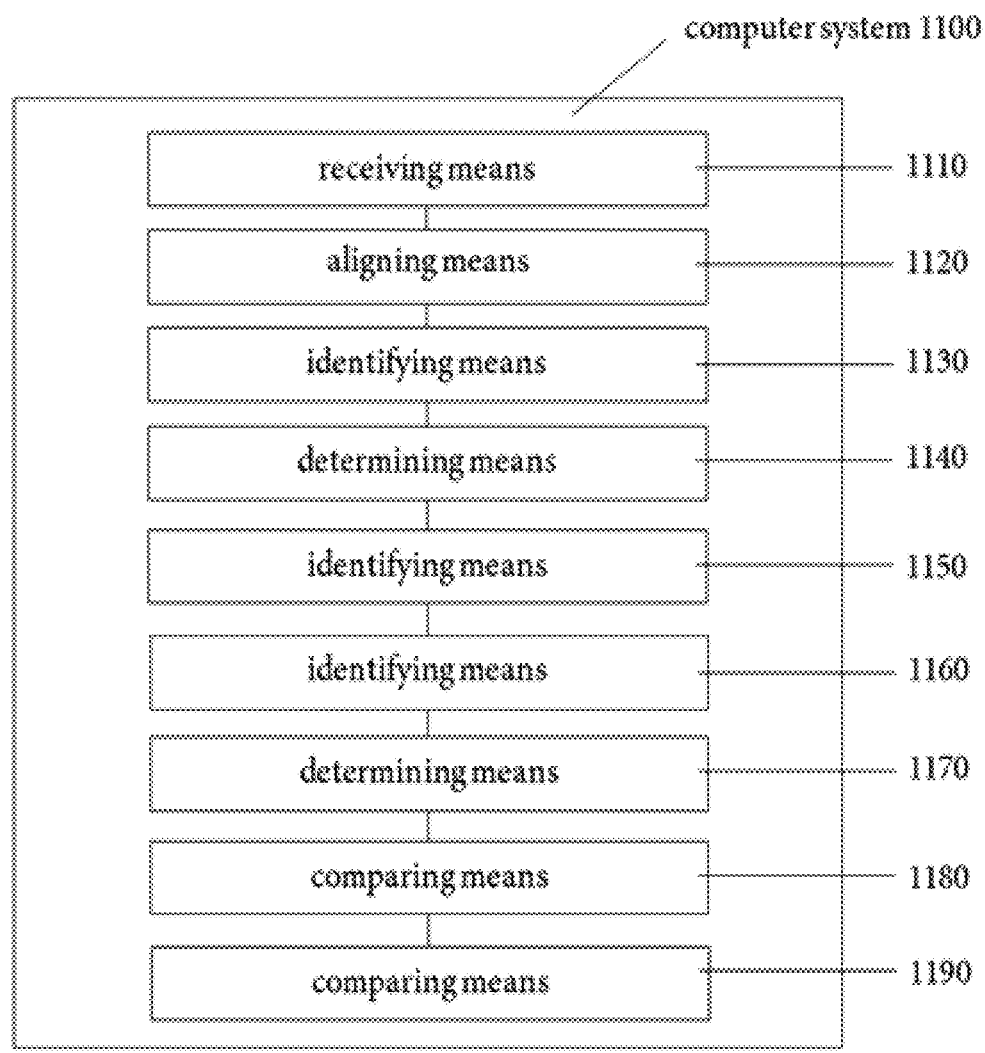
FIG. 15A is an example of a general block diagram showing the relation between software and hardware resources that may be used to implement the methods and systems of the invention.

Referring to FIG. 15A, computer system 1100 may comprise receiving means 1110 for example for receiving data obtained from a plurality of sequencing reads, aligning means 1120 for aligning the plurality of sequence reads to the target region of the reference sequence, identifying means 1130 for identifying a first candidate variant having a first allele at a first location of the target region based on sequence reads of the first sample differing from a reference allele at the first location of the reference sequence, determining means 1140 for determining a first variant frequency for the first allele at the first location based on sequence reads of the first sample that align to the first location of the reference sequence, identifying means 1150 for identifying the first candidate variant as corresponding to a first variant class selected from a plurality of variant classes, each variant class of the plurality of variant classes corresponding to a different type of variant, further identifying means 1160 for identifying a set of second locations in the target region of the reference sequence that have the reference allele, wherein at least 50% of the other locations in the one or more samples exhibit a false positive for the first allele, and wherein the set of second locations includes the first location, further determining means 1170 for determining at each of the set of second locations and for each of the one or more samples a second variant frequency of the first allele based on sequence reads of the sample that align to the second location of the reference sequence, the second variant frequencies forming a statistical distribution and comparing means 1180 for comparing the first variant frequency to a statistical value of the statistical distribution to determine a probability value of the first variant frequency relative to the statistical value of the statistical distribution, and further comparing means 1190 for comparing the probability value to a threshold value as part of determining whether the first candidate variant is a true positive in the first sample for the first allele, the threshold value differentiating between false positives and true positives for the first allele.

Figure 15B:
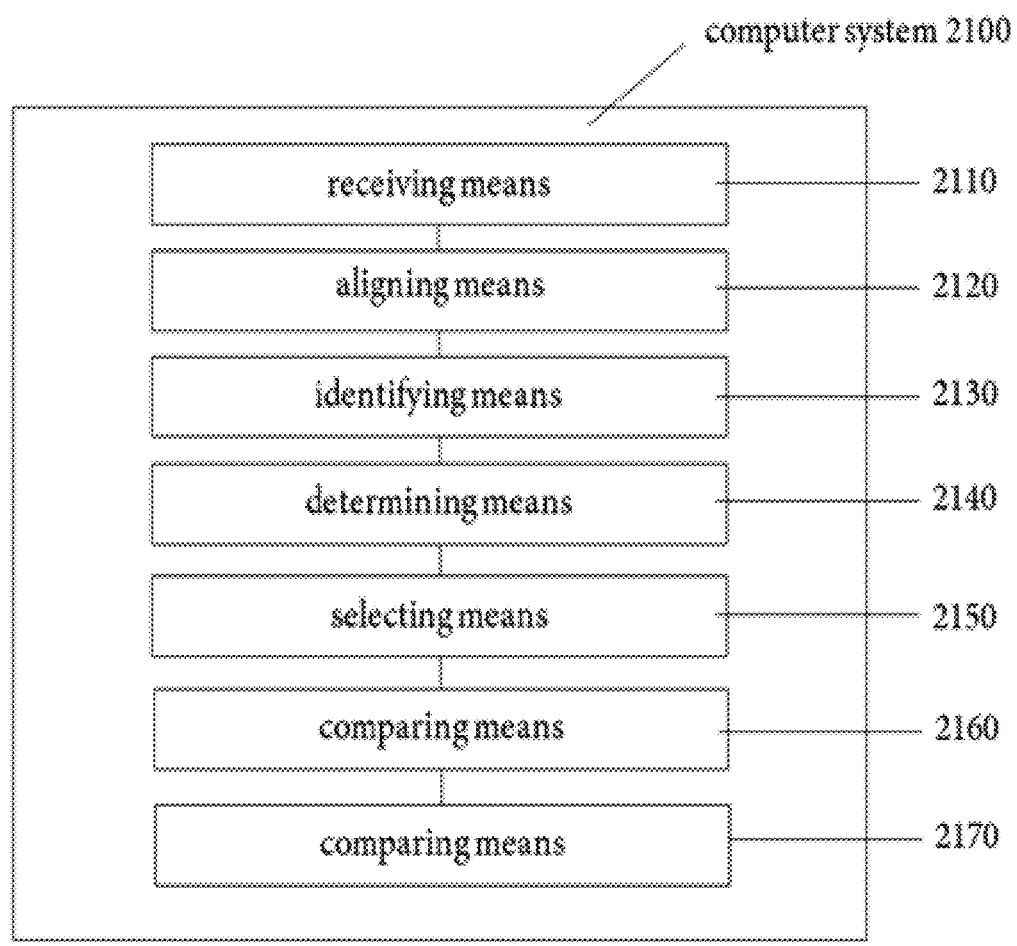
FIG. 15B is another example of a general block diagram showing the relation between software and hardware resources that may be used to implement the methods and systems of the invention.

Referring to FIG. 15B, computer system 2100 may comprise receiving means 2110 for example for receiving data obtained from a plurality of sequencing reads, aligning means 2120 for aligning the plurality of sequence reads to the target region of the reference sequence, identifying means 2130 for identifying whether the first allele exists at the first location in each sample of the at least two samples based on aligned sequence reads of each sample at the first location differing from a reference allele at the first location of the reference sequence, determining means 2140 for determining a variant count of the first allele at the first location and a wild type count of the reference allele at the first location for each sample of the at least two samples, selecting means 2150 for selecting, from the at least two samples, at least one sample as a reference sample, comparing means 2160 for comparing a first variant count of the first allele at the first location and a first wild type count of the reference allele at the first location for the first sample to a second variant count of the first allele at the first location and a second wild type count of the reference allele at the first location for the reference sample to determine a probability value of the variant having the first allele at the first location for the first sample, and further comparing means 2170 for comparing the probability value to a threshold value as part of determining whether the first allele at the first location in the first sample is a true positive for the first allele, the threshold value differentiating between false positives and true positives for the first allele at the first location. In certain embodiments, the system may also comprise displaying means for displaying the results on a computer screen.

Figure 14:
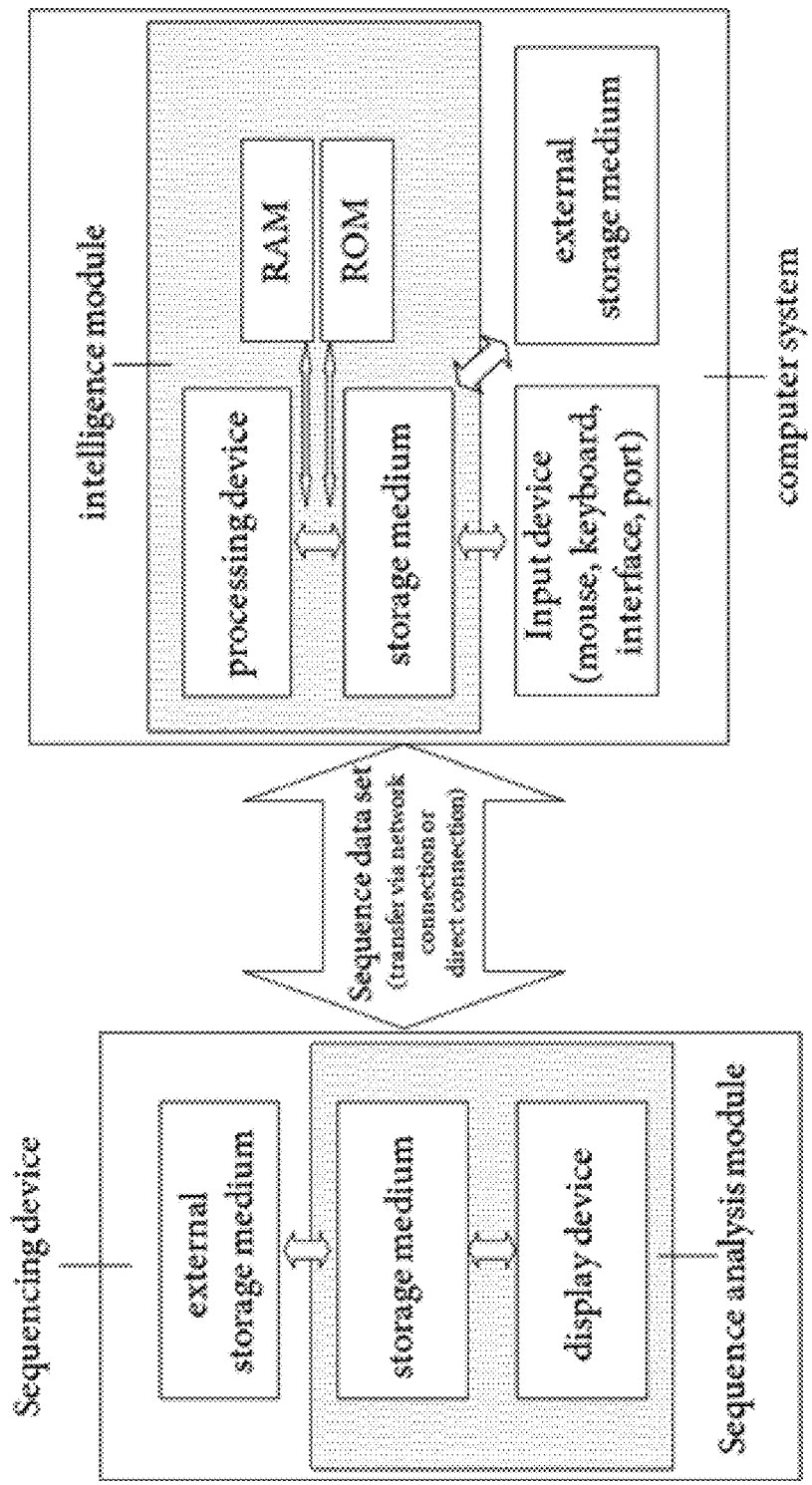
FIG. 14 is an example of a general block diagram showing the relation between a sequencing device and a computer system.

FIG. 14 further illustrates the interaction between the sequencing device and the computer system. The system comprises a sequence analysis module which may be located in a sequencing device and an intelligence module which is part of the computer system. The data sets (sequencing data sets) are transferred from the analysis module to the intelligence module or vice versa via a network connection or a direct connection. The data sets may be processed according to FIG. 15A or 15B by computer code running on the processor and being stored on the storage device of the intelligence module and after processing transferred back to the storage device of the analysis module, where the modified data may be displayed on a displaying device. In some embodiments, the intelligence module may also be implemented in the sequencing device.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned herein are incorporated by reference in their entirety for all purposes. None is admitted to be prior art.

What is claimed is:

1. A computer-implemented method of detecting low frequency variants in a target region in a first sample, the method comprising, using a computer system:
   sequencing DNA fragments from one or more samples, the one or more samples including the first sample, wherein the sequencing includes targeting the target region in the DNA fragments, and wherein the sequencing is associated with an error rate;
   receiving a plurality of sequence reads obtained from sequencing the DNA fragments from the one or more samples;
   aligning the plurality of sequence reads to the target region of a reference sequence;
   identifying a first candidate variant having a first allele at a first location of the target region based on sequence reads of the first sample differing from a reference allele at the first location of the reference sequence;
   determining a first variant frequency for the first allele at the first location based on sequence reads of the first sample that align to the first location of the reference sequence, wherein the first variant frequency is equal to or lower than the error rate;

identifying the first candidate variant as corresponding to a first variant class selected from a plurality of variant classes, each variant class of the plurality of variant classes corresponding to a different type of variant;

identifying a set of second locations in the target region of the reference sequence that have the reference allele, wherein at least 50% of the other locations in the one or more samples exhibit a false positive for the first allele, and wherein the set of second locations includes the first location;

at each of the set of second locations and for each of the one or more samples:

determining a second variant frequency of the first allele based on sequence reads of the sample that align to the second location of the reference sequence, the second variant frequencies forming a statistical distribution;

comparing the first variant frequency to a statistical value of the statistical distribution to determine a probability value of the first variant frequency relative to the statistical value of the statistical distribution; and determining whether the first candidate variant is a true positive in the first sample for the first allele by comparing the probability value to a threshold value, the threshold value differentiating between false positives and true positives for the first allele.

2. The computer-implemented method of claim 1, wherein the reference sequence corresponds to a consensus sequence as determined from normal cells.

3. The computer-implemented method of claim 1, wherein the one or more samples are derived from cell-free DNA fragments.

4. The computer-implemented method of claim 1, wherein the one or more samples are derived from RNA of a biological sample.

5. The computer-implemented method of claim 1, wherein the one or more samples are sequenced in a single sequencing run.

6. The computer-implemented method of claim 1, wherein the statistical value of the statistical distribution includes a mean value.

7. The computer-implemented method of claim 1, wherein the probability value is a z-score, modified z-score, cumulative probability, Phred quality score, or modified Phred quality score.

8. The computer-implemented method of claim 1, wherein the statistical distribution is a statistical distribution of logarithmic transformations of the second variant frequencies.

9. The computer-implemented method of claim 1, wherein the threshold value is determined using support vector machines classifier based on training data obtained from one or more sequencing runs.

10. The computer-implemented method of claim 1, wherein the threshold value is a function of variant frequency.

11. The computer-implemented method of claim 1, wherein the first variant frequency is equal to or lower than 1%.

* * * * *